US009320795B2

(12) United States Patent
Mathers et al.

(10) Patent No.: US 9,320,795 B2
(45) **Date of Patent: *Apr. 26, 2016**

(54) BACTERIOPHAGE PREPARATIONS AND METHODS OF USE THEREOF

(75) Inventors: Jeremy Mathers, Tinley Park, IL (US); Alexander Sulakvelidze, Towson, MD (US)

(73) Assignees: Zoctis Server LLC, Florham Park, NJ (US); Intrlytix Inc, Baltimore, MD (US)

( * ) Notice: Subject to any disclaimer, the term of this patent is extended or adjusted under 35 U.S.C. 154(b) by 872 days.

This patent is subject to a terminal disclaimer.

(21) Appl. No.: 12/660,576

(22) Filed: Mar. 1, 2010

(65) Prior Publication Data

US 2010/0297086 A1 Nov. 25, 2010

Related U.S. Application Data

(63) Continuation-in-part of application No. 12/334,863, filed on Dec. 15, 2008, now Pat. No. 8,956,628.

(60) Provisional application No. 61/013,325, filed on Dec. 13, 2007.

(51) Int. Cl.

| | |
|---|---|
| ***A61K 35/76*** | (2015.01) |
| ***C12N 7/00*** | (2006.01) |
| ***A61K 45/06*** | (2006.01) |

(52) U.S. Cl.

CPC ................. *A61K 45/06* (2013.01); *A61K 35/76* (2013.01); *C12N 7/00* (2013.01); *C12N 2795/00032* (2013.01)

(58) Field of Classification Search

CPC .................... A61K 35/76; C12N 2795/00032; C12N 2795/00051; C12N 7/00

USPC ........................................... 424/203.1, 247.1

See application file for complete search history.

(56) References Cited

U.S. PATENT DOCUMENTS

| | | | | |
|---|---|---|---|---|
| 6,461,608 | B1 | 10/2002 | Averback et al. | |
| 7,211,426 | B2 | 5/2007 | Bruessow et al. | |
| 7,332,307 | B2 | 2/2008 | Carlton et al. | |
| 7,371,375 | B2 * | 5/2008 | Zimmer et al. | 424/94.1 |
| 7,459,272 | B2 | 12/2008 | Morris et al. | |
| 7,625,739 | B2 * | 12/2009 | Pasternack et al. | 435/235.1 |
| 8,956,628 | B2 * | 2/2015 | Mathers et al. | 424/247.1 |
| 2003/0180319 | A1 | 9/2003 | Burden et al. | |
| 2005/0153415 | A1 | 7/2005 | Zimmer et al. | |
| 2007/0054357 | A1 | 3/2007 | Pasternack et al. | |
| 2007/0190033 | A1 | 8/2007 | Soothill et al. | |
| 2007/0292397 | A1 | 12/2007 | McNulty et al. | |
| 2008/0038322 | A1 | 2/2008 | Murthy et al. | |
| 2008/0118468 | A1 | 5/2008 | Sulakvelidze et al. | |
| 2008/0194000 | A1 | 8/2008 | Pasternack et al. | |
| 2008/0254009 | A1 | 10/2008 | Finegold et al. | |
| 2008/0260697 | A1 | 10/2008 | Murthy et al. | |
| 2008/0311643 | A1 | 12/2008 | Sulakvelidze et al. | |
| 2008/0318311 | A1 | 12/2008 | Murthy et al. | |
| 2009/0042754 | A1 | 2/2009 | Okazaki | |
| 2009/0047726 | A1 | 2/2009 | Pasternack et al. | |
| 2009/0047727 | A1 | 2/2009 | Pasternack et al. | |

OTHER PUBLICATIONS

Arakawa et al Poult. Sci. Jul. 1975 vol. 54 No. 4 1000-1007.*
Smith HW (J.Gen. Microbiol. 21622-630, 1959).*
Zimmer, Marcus, et al. Genomic analysis of Clostridium perfringens bacteriophage 3626 . . . J. Bacteriology (2002) 184(16) pp. 4359-4368.
Schijven, J.F., et al. Bacteriophage and Clostridium spores as indicator organisms for removal of pathogens. Water Res. (2003) 37 pp. 2186-2194.
Smith, H. Williams, The bacteriophages of clostridium perfringens, J. Gen. Microbiol. (1959) 21 pp. 622-630.
Tellez, Guillermo, et al., Evidence for Clostridium septicum as the primary cause of cellulitis in commercial turkeys, J. Vet. Diagn. Invest. (2009) 21 pp. 374-377.
Songer, J. Glenn, Clostridial enteric disease of domestic animals, Clin. Microbio. Rev. (1996) 9(2) pp. 216-234.

* cited by examiner

*Primary Examiner* — Padma V Baskar
(74) *Attorney, Agent, or Firm* — G Kenneth Smith

(57) ABSTRACT

Disclosed herein are purified bacteriophage preparations that effectively lyse a plurality of *Clostridium* species strains, in particular *C. perfringens, C. septicum* and *C. difficile*. In one embodiment, a purified bacteriophage preparation includes four or more *C. perfringens*-specific bacteriophage, wherein each bacteriophage has lytic activity against at least five *Clostridium* species strains. In another embodiment, the purified bacteriophage preparation includes five or more *C. perfringens*-specific bacteriophage. The invention also relates to the use of purified bacteriophage preparation in combination with antibiotics for the treatment of animals including poultry. The invention also relates to the use of the purified bacteriophage preparations as treatments effective against antibiotic-resistant strains of *Clostridium.*

11 Claims, 6 Drawing Sheets

**5.2.1 PFGE analysis of *C. perfringens* chromosomal DNA digested with *SmaI*.**

Lanes 1, 15, 30, 31, 39 and 47 – λ ladder PFGE marker; Lanes 2-14: Cp1-Cp13; Lanes 16-21: Cp14-Cp19; Lanes 22-29: Cp21-Cp28; Lanes 32-38: Cp29-Cp35; Lanes 40-46: Cp36-Cp42.

Dendrogram portraying the genetic diversity of various *C. perfringens* strains based on *SmaI*-digested PFGE patterns of *C. perfringens* DNA.

CPLV-42

CPAS-15

CPAS-16

CPTA-37

CPAS-7

BACTERIOPHAGE PREPARATIONS AND METHODS OF USE THEREOF

CROSS REFERENCE OF RELATED PATENT APPLICATIONS

This application is a continuation-in-part of U.S. patent application Ser. No. 12/334,863 filed on Dec. 15, 2008 now U.S. Pat. No. 8,956,628 which claims priority to U.S. Provisional Application Ser. No. 61/013,325 filed on Dec. 13, 2007, both of which are incorporated in their entirety by reference herein.

BACKGROUND

Antibiotic use enhances the growth of healthy domesticated poultry and livestock. Although extensive bans and restrictions have not been implemented in the United States as they have in the E.U. and other countries, pressure for antibiotics alternatives has increased due to concerns of increasing antibiotic resistance among food borne bacteria. Banning or markedly reducing the agricultural and farm-veterinary use of antibiotics may have a profound negative impact on the safety of foods and on the treatment of sick flocks or herds of domesticated livestock, however. Thus, effective, safe and environmentally friendly alternative(s) to antibiotics are needed to address these concerns and needs.

Viruses that kill bacteria were first identified in the early part of the 20th century by Frederick Twort and Felix d'Herelle who called them bacteriophages or bacteria-eaters (from the Greek phago meaning to eat or devour). Because of their remarkable antibacterial activity, phages were used to treat disease of economically important animals/domesticated livestock almost immediately after their discovery, and therapeutic applications for humans closely followed. However, with the advent of antibiotics, phage therapy gradually fell out-of-favor in the United States and Western Europe, and virtually no subsequent research was done on the potential therapeutic application of phages for bacterial diseases of humans or animals. The emergence of antibiotic-resistance in bacteria, however, has rekindled interest in therapeutic bacteriophages. Phage therapy may have a positive impact on human health by improving the safety of foods in the U.S.A. and elsewhere, and by helping to reduce safely the use of antibiotics in agribusiness.

Among the bacteria that cause significant morbidity and mortality in chickens, *C. perfringens* is one of the most notorious pathogens. In chicken *C. perfringens* infections are often manifested as necrotic enteritis that occur later in the production cycle, often following a coccidial infection or other insult to the gastrointestinal tract. It is thus desirable to develop bacteriophage preparations suitable to reduce morbidity and mortality in chickens.

*C. septicum* is an anaerobic bacterium which causes or contributes to gas gangrene and malignant edema in animals and people, usually following direct contact of a traumatic wound. *C. septicum* multiplies locally and disseminates throughout the animal's body, producing local lesions and signs of toxemia (Songer, 1996). Specifically for turkeys and chickens, *C. septicum* is implicated in gangrenous dermatitis (or cellulitis), an economically important disease (Tellez et al., 2009; NTF, 2007). Typically, antibiotics are used to treat or prevent *C. septicum* infections in poultry (Songer, 1996, NTF, 2007).

*Clostridium difficile* is well established as a pathogen of horses, calves, and pigs, as well as poultry. *Clostridium difficile* is a normal inhabitant of the gastrointestinal tract of many species of mammals and has been isolated from bird feces; it is the most common pathogenic enteric clostridial organism in humans.

SUMMARY

Disclosed herein are purified bacteriophage preparations that effectively lyse a plurality of strains of a *Clostridium* species. In one embodiment, a purified bacteriophage preparation comprises four or more *C. perfringens*-specific bacteriophage, wherein each bacteriophage has lytic activity against at least five strains of a *Clostridium* species. In another embodiment, the purified bacteriophage comprises five or more *C. perfringens*-specific bacteriophage. The bacteriophage preparations are effective against both antibiotic susceptible and antibiotic-resistant strains of *Clostridium* including *C. perfringens, C. septicum* and *C. difficile.*

Disclosed herein are purified bacteriophage preparations that effectively lyse a plurality of *C. perfringens* strains. In one embodiment, a purified bacteriophage preparation comprises four or more *C. perfringens*-specific bacteriophage, wherein each bacteriophage has lytic activity against at least five *C. perfringens* strains. In another embodiment, the purified bacteriophage comprises five or more *C. perfringens*-specific bacteriophage.

Disclosed herein are purified bacteriophage preparations that effectively lyse a plurality of *C. septicum* strains. In one embodiment, a purified bacteriophage preparation comprises four or more *C. perfringens*-specific bacteriophage, wherein each bacteriophage has lytic activity against at least five *C. septicum* strains. In another embodiment, the purified bacteriophage comprises five or more *C. perfringens*-specific bacteriophage.

Disclosed herein are purified bacteriophage preparations that effectively lyse a plurality of *C. difficile* strains. In one embodiment, a purified bacteriophage preparation comprises four or more *C. perfringens*-specific bacteriophage, wherein each bacteriophage has lytic activity against at least five *C. septicum* strains. In another embodiment, the purified bacteriophage comprises five or more *C. perfringens*-specific bacteriophage.

In another embodiment, a method of reducing chicken mortality due to *C. perfringens* infections comprises administering a purified bacteriophage preparation four or more *C. perfringens*-specific bacteriophage, wherein each bacteriophage has lytic activity against at least five strains of a *Clostridium* species including but not limited to *C. perfringens, C. septicum* or *C. difficile.*

In another embodiment, a method of selecting a *C. perfringens* host strain suitable to propagate bacteriophage from a plurality of test strains comprises microbiologically confirming one test strain from the plurality of test strains as a *C. perfringens* species to produce a confirmed strain; associating the confirmed strain with a poultry disease to produce a disease-associated strain; and applying one or more additional selective criterion to the disease-associated strain selected from minimal antibiotic resistance and absence of animal-virulence markers other than for *C. perfringens* to produce the *C. perfringens* host strain suitable to propagate bacteriophage.

In yet another embodiment, a method of producing a bacteriophage cocktail comprises mixing four or more *C. perfringens*-specific bacteriophage, wherein each bacteriophage has lytic activity against at least five strains of a *Clostridium* species including but not limited to *C. perfringens, C. septicum* or *C. difficile.*

The present invention also relates to the use of bacteriophage preparations in combination with antibiotics. The bacteriophage preparations when used in combination with antibiotics against *Clostridium* species preferably *C. perfringens, C. septicum*, or *C. difficile* which cause necrotic enteritis, gangrenous dermatitis, cellulitis, or enteric diarrheal diseases provide complementary (additive and/or synergistic) lytic activity. The bacteriophage preparations of the present invention can be combined with antibiotic preparations to make a single composition for administration to animals for growth enhancement and/or therapeutic purposes.

Figure 1:
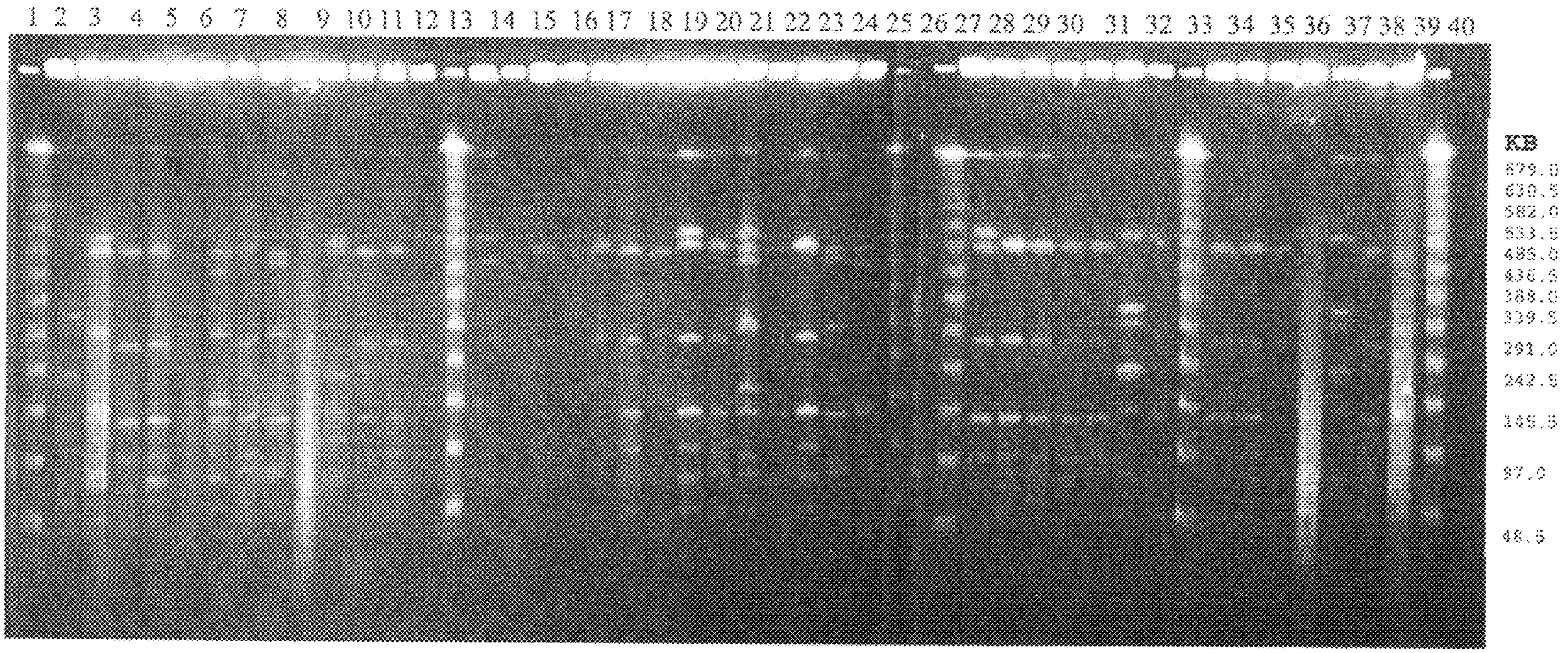
FIG. 1 shows a phylogenetic analysis of *C. perfringens* strains.

The above-described and other features will be appreciated and understood by those skilled in the art from the following detailed description, drawings, and appended claims.

DETAILED DESCRIPTION

Disclosed herein are purified bacteriophage preparations that effectively lyse a plurality of *Clostridium* species strains including *C. perfringens, C. septicum* or *C. difficile*. Lysis of particular strains is demonstrated by the drop-on-lawn method, which is standard in the art. The bacteriophage preparations are suitable to reduce morbidity and mortality in chickens.

In one embodiment, a purified bacteriophage preparation comprises four or more *C. perfringens*-specific bacteriophage, wherein each bacteriophage has lytic activity against at least five *C. perfringens* strains. In another embodiment, the purified bacteriophage comprises five or more *C. perfringens*-specific bacteriophage.

In one embodiment, a purified bacteriophage preparation comprises four or more *C. perfringens*-specific bacteriophage, wherein each bacteriophage has lytic activity against at least five *C. septicum* strains. In another embodiment, the purified bacteriophage comprises five or more *C. perfringens*-specific bacteriophage.

In one embodiment, the bacteriophage preparation comprises CPAS-12 (accession number PTA-8479), CPAS-15 (accession number PTA-8480), CPAS-16 (accession number PTA-8481) and CPLV-42 (accession number PTA-8483). In another embodiment, the bacteriophage preparation consists essentially of CPAS-12, CPAS-15, CPAS-16 and CPLV-42. In yet another embodiment, the bacteriophage preparation consists of CPAS-12, CPAS-15, CPAS-16 and CPLV-42.

In another specific embodiment, the bacteriophage preparation comprises CPAS-7 (accession number PTA-8478), CPAS-12, CPAS-15, CPAS-16 and CPLV-42 (accession number PTA-8483). In another embodiment, the bacteriophage preparation consists essentially of CPAS-7, CPAS-12, CPAS-15, CPAS-16 and CPLV-42. In yet another embodiment, the bacteriophage preparation consists of CPAS-7, CPAS-12, CPAS-15, CPAS-16 and CPLV-42.

In one embodiment, the *C. perfringens* strains are ATCC strain 25768, ATCC strain 3624, ATCC strain 9856, ATCC strain 3628, ATCC strain 13124, ATCC strain PTA-8495, NRRL strain B-50143, NRRL strain B-50144, NRRL strain B-50145, and combinations comprising one or more of the foregoing strains. In a specific embodiment, the at least five *C. perfringens* strains comprise ATCC strain 3624 and ATCC strain 9856.

In one embodiment, the bacteriophage preparations are characterized by their specificity and effectiveness against *C. perfringens* strains. In one embodiment the purified bacteriophage preparation lyses greater than or equal to 85% of at least 40 screened *C. perfringens* strains, wherein the bacteriophage preparation is incapable of infecting at least 10 strains of *E. coli, L. monocytogenes, S. enteric* and *P. aeruginosa*. In another embodiment the purified bacteriophage preparation lyses greater than or equal to 85% of at least 45 screened *C. perfringens* strains. In yet another embodiment, each of the individual *C. perfringens*-specific bacteriophage lyses 15% to 90% of the screened *C. perfringens* strains.

In one embodiment, the bacteriophage preparations are characterized by their specificity and effectiveness against *C. septicum* strains. In one embodiment the purified bacteriophage preparation fully or partially lyses greater than or equal to 85% of at least 7 screened *C. septicum* strains, wherein the bacteriophage preparation is incapable of infecting at least 10 strains of *E. coli, L. monocytogenes, S. enteric* and *P. aeruginosa*. In another embodiment the purified bacteriophage preparation fully lyses greater than or equal to 25% of at least 7 screened *C. septicum* strains. In yet another embodiment, each of the individual *C. perfringens*-specific bacteriophage lyses 15% to 90% of the screened *C. septicum* strains.

The present invention also relates to the use of bacteriophage preparations in combination with antibiotics. The bacteriophage preparations when used in combination with antibiotics against *Clostridium* species preferably *C. perfringens, C. septicum*, or *C. difficile* which cause necrotic enteritis, gangrenous dermatitis, cellulitis, or enteric diarrheal diseases provide complementary (additive and/or synergistic) lytic activity. In one embodiment the bacteriophage preparations could be applied to animals also being administered antibiotics for growth enhancement and/or therapeutic purposes. In another embodiment the bacteriophage preparations can be combined with the antibiotics in a single preparation provided to animals for growth enhancement and/or therapeutic purposes.

The bacteriophage preparations are effective against both antibiotic susceptible and antibiotic-resistant strains of *Clostridium* including *C. perfringens, C. septicum* and *C. difficile*. Agricultural or medical strains having natural tolerance or acquired resistance to antibiotics, may have reduced therapeutic effectiveness if treated with the same or similar antibiotic classes to which they are tolerant, but would be predicted to be more susceptible to the phage cocktail INT-401 if an animal or person were alternatively or concurrently treated with INT-401. This pattern may allow a) enhanced killing or inhibition of disease causing *Clostridium* spp. in animals or humans if combined, b) rotating or strategically dosing different levels of treatment of antibiotics and phage in order to efficiently reduce or eliminate the total burden of disease-causing *Clostridium* spp. in the animal or person's gastrointestinal tract at different disease stages or animal/human ages. Concurrent treatment of antibiotics plus bacteriophage could allow enhancement of killing or inhibitory action of disease-causing bacteria, as well as reducing the likelihood of independent phage or antibiotic resistance selection due to their different and complementary modes of action, in animals or people.

The bacteriophage preparations of the present invention, preferably INT-401, can lyse greater than 25% of bacitracin resistant and/or macrolide-resistant (tylosin-resistant) strains of *C. perfringens*. The bacteriophage preparations of the present invention can lyse greater than 50% of bacitracin resistant and/or macrolide-resistant (tylosin-resistant) strains of *C. perfringens*. The bacteriophage preparations of the present invention can lyse antibiotic-resistant bacteria to the same or greater degree as antibiotic-susceptible types.

The term "purified" in reference to a bacteriophage or bacteriophage preparation does not require absolute purity (such as a homogeneous preparation). Instead, it is an indication that the bacteriophage or bacteriophage preparation is relatively more pure than in the natural environment (compared to the natural level, this level should be at least 2-5 fold greater, e.g., in terms of mg/mL). Purification is according to any method known to those of ordinary skill in the art that will result in a preparation of bacteriophage substantially free from other nucleic acids, proteins, carbohydrates, lipids, or subcellular organelles. Individual bacteriophage may be purified to electrophoretic homogeneity. Purification of at least one order of magnitude, preferably two or three orders, and more preferably four or five orders of magnitude is expressly contemplated.

Purity of phage stocks can be determined by pulsed-field gel electrophoresis (PFGE) of uncut DNA. In one embodiment, approximately 100-200 ng of the phage DNA is electrophoresed in a 1% SeaKem Gold Agarose (Cambrex, Rockland, Me.) gel with 0.5× Sodium boric acid (1×SB: 10 mM sodium hydroxide pH adjusted to 8.5 with boric acid) buffer at 14° C. in a CHEF Mapper XA PFGE apparatus (Bio-Rad Laboratories, Hercules, Calif.). The run time is 12 hours with a voltage of 6 V/cm and a linearly ramped pulse time of 0.06 s to 8.53 seconds. The gels were stained with ethidium bromide and visualized with UV light.

In one embodiment, endotoxin levels for lots of phage produced are determined by a *Limulus* amoebocyte lysate (LAL) assay using a chromogenic assay (QCL-1000 Kit, BioWhittaker, Walkersville, Md.) following manufacturers' recommendations. A standard curve with *E. coli* endotoxin (supplied with kit) ranging from 0.1 to 1.0 endotoxin units (EU) per milliliter endotoxin is constructed for each assay by plotting the optical density at 405 nm ($OD_{405}$) versus EU/ml. Phage samples are assayed diluted in sterile water (USP, Baxter, Deerfield, Ill.) and the absorbance at 405 nm was measured with a μQuant (Bio-Tek Instruments, Inc., Winooski, Vt.) microplate reader. Endotoxin concentrations for each sample are calculated by linear regression from the standard curve. Standards and samples are analyzed in triplicate.

In one embodiment, carbohydrate content for all lots of phage produced is determine by an anthrone method. A standard curve with glucose ranging from 10 to 250 μg/ml is constructed for each assay by plotting optical density at 625 nm ($OD_{625}$) versus μg/ml glucose concentration. Phage samples are assayed in PBS and the absorbance at 625 nm was measured with a μQuant (Bio-Tek Instruments, Inc., Winooski, Vt.) microplate reader. Carbohydrate concentrations for each sample are calculated by linear regression from the standard curve. Standards and samples are analyzed in triplicate.

In one embodiment, the total protein content for all lots of phage produced is determine by a bicinchoninic acid (BCA) assay using a colorometric assay (BCA™ Protein Assay kit, Pierce, Rockford, Ill.) following manufacturers' recommendations. A standard curve with bovine serum albumin ranging from 20 to 2000 μg/ml protein is constructed for each assay by plotting optical density at 562 nm ($OD_{562}$) versus μg/ml BSA. The absorbance at 562 nm was measured with a μQuant (Bio-Tek Instruments) microplate reader. Total protein concentrations for each sample are calculated by linear regression from the standard curve. Standards and samples are analyzed in triplicate.

The term "strain" means bacteria or bacteriophage having a particular genetic content. The genetic content includes genomic content as well as recombinant vectors. Thus, for example, two otherwise identical bacterial cells would represent different strains if each contained a vector, e.g., a plasmid, with different phage open reading frames.

By "treatment" or "treating" is meant the administering a bacteriophage preparation for prophylactic and/or therapeutic purposes. The term "prophylactic treatment" refers to treating an animal that is not yet infected but is susceptible or otherwise at risk of a bacterial infection. The term "therapeutic treatment" refers to administering treatment to an animal already suffering from infection.

The term "bacterial infection" means an invasion of the host organism, animal or plant, by pathogenic bacteria. This includes excessive growth of bacteria which are normally present in or on the body of an organism, but more generally, a bacterial infection is any situation in which the presence of a bacterial population(s) is damaging to a host organism. Thus, for example, an organism suffers from a bacterial infection when excessive numbers of a bacterial population are present in or on the organism's body, or when the effects of the presence of a bacterial population(s) is damaging to the cells, tissue, or organs of an organism.

The terms "administer", "administering", and "administration" refer to a method of giving a dosage of a bacteriophage preparation to an organism. Suitable methods include topical, oral, intravenous, transdermal, intraperitoneal, intramuscular, or intrathecal. The preferred method of administration varies depending on various factors, e.g., the components of the bacteriophage preparation, the site of potential or actual bacterial infection, the bacterium involved, and the infection severity.

In the context of treating a bacterial infection a "therapeutically effective amount" or pharmaceutically effective amount" indicates an amount of a bacteriophage preparation which has a therapeutic effect. This generally refers to the inhibition, to some extent, of the normal cellular functioning of bacterial cells that render or contribute to bacterial infection.

The doses of bacteriophage preparation that is useful as a treatment is a "therapeutically effective amount". Thus, as used herein, a therapeutically effective amount means an amount of a bacteriophage preparation that produces the desired therapeutic effect as judged by clinical trial results. This amount can be routinely determined by one skilled in the art and will vary depending on several factors, such as the particular bacterial strain involved and the particular bacteriophage preparation used.

In one embodiment, a bacteriophage preparation optionally includes one or more pharmaceutically acceptable excipients. In one embodiment, the excipient is a water-conditioning agent, for example agent suitable for water dechlorination and/or phage stabilization. Such agents are innocuous to the bacteriophage cocktail, but when added prior to or simultaneously with *C. perfringens* bacteriophage or bacteriophage cocktails, act to dechlorinate municipal levels of chlorine, which if untreated would kill or significantly reduce the viability of the bacteriophage or bacteriophage cocktail. Exemplary water-conditioning agents include amino acids and/or salts which help to normalize the pH and ionic balance of the bacteriophage cocktail, when added to diverse water sources used for the animal's drinking and for phage delivery. In one embodiment, the water-conditioning agent is a 50 mM citrate-phosphate-thiosulfate (CPT) buffer, comprising 40 mg sodium thiosulfate, 6.0 gm disodium phosphate (anhydrous), 1.1 gm citric acid (anhydrous) per liter deionized water pH 7.0. By including water-conditioning agents in the cocktail or adding separately to the treatment water, the water-conditioning agents act to both stabilize and protect the bacteriophage cocktail in a commercial preparation suitable for routine field use.

A method of producing a bacteriophage cocktail comprises mixing four or more *C. perfringens*-specific bacteriophage, wherein each bacteriophage has lytic activity against at least five *C. perfringens* strains. In another embodiment, a method of producing a bacteriophage cocktail comprises mixing five or more *C. perfringens*-specific bacteriophage wherein each bacteriophage has lytic activity against at least five *C. perfringens* strains.

Once *C. perfringens* cocktail have been selected, further testing can be employed to refine the specificity of the cocktail. In one embodiment, a bacteriophage cocktail is tested against additional *C. perfringens* strains which have antibiotic resistance genes to test the phage cocktail against antibiotic-resistant strains and evaluate the cocktail's potential use in the field against antibiotic-resistant Clostridia. In another embodiment, a bacteriophage cocktail is tested against *C. perfringens* strains derived from other animal species other than chickens to further evaluate and define the host range of the strain or strains to include additional animal species (e.g., swine, cattle, turkey, sheep, exotics, dogs, cats and the like). In another embodiment, a bacteriophage cocktail is tested against *Clostridium* of different species (i.e., other than *C. perfringens* such as but not limited to *C. perfringens, C. septicum* and *C. difficile*. In yet another embodiment, a bacteriophage cocktail is tested against additional gram-positive bacteria (e.g., both reference strains and animal-associated types, aerobic and anaerobic) to further evaluate and define the host range. In another embodiment, a bacteriophage cocktail is tested against additional gram-negative and gram-variable bacteria to further evaluate host range. In another embodiment, a bacteriophage cocktail is tested for pre-conditioning or additive formulations, using different levels of stabilizing and dechlorinating water-conditioning agents, for optimally maintaining the viability of the phage cocktail under a wide range of water types and chlorination levels as may be expected in field usage conditions.

In another embodiment, the method further comprises testing the potential of the bacteriophage cocktail for the development of intrinsic phage resistance in the target host. Testing includes challenging test *C. perfringens, C. septicum* and/or *C. difficile* as well as other *Clostridium* species host strains with individual and/or combined bacteriophage cocktail phage over several cycles, and ascertaining the rate of resistance development toward the individual phages as well as that of the combination(s) of phages. It is anticipated that the combination bacteriophage cocktail will have significantly less development of resistance against a given individual host strain. An optimum combination of bacteriophages may be further elucidated using known mathematical optimization techniques or software packages (Box-Hunter, Latin Squares, Taguchi, Simplex, etc.) as applied to the bacteriophage resistance data generated from such experimentation.

Advantages of bacteriophage therapy include high bactericidal activity, high selectivity permitting targeting of specific pathogens while leaving desirable bacterial flora intact, specifically for prokaryotic cells, and environmental benignity. In livestock and poultry applications, bacteriophage have the advantage of specificity that should not select for phage-resistance in non-targeted bacterial species, the possible emergence of resistance against phages will not affect the susceptibility of the bacteria to antibiotics used to treat humans, and unlike antibiotics, phage preparations can readily be modified in response to changes in bacterial pathogen populations or susceptibility.

The poultry and livestock industries use antibiotics for three main purposes: (i) prophylactic ally, to prevent disease in flocks, herds, etc., (ii) to treat sick livestock, and (iii) to improve digestion and utilization of feed, which often results in improved weight gain. Antibiotics used in the latter setting are often referred to as "growth-promoting antibiotics" or GPAs. Most GPAs are not commonly used in human medicine, and they are usually administered, in small amounts, to poultry and other livestock via food. Bacteriophages can effectively replace and/or reduce the use of antibiotics in all three of the above-mentioned settings.

Among the bacteria that cause significant morbidity and mortality in chickens, *C. perfringens* is one of the most notorious pathogens. In order to identify effective bacteriophage for a generically diverse population of *C. perfringens* strains, isolates of *C. perfringens* were first identified. In order to identify effective bacteriophage, it is useful to identify *C. perfringens* strains that affect poultry at various locations within the United States. As shown herein, forty-one strains of *C. perfringens* were isolated from various sources and characterized by pulsed-filed gel electrophoresis (PFGE) typing. (FIG. 1) Among the 35 strains subjected to PFGE, phylogenetic analysis showed that these strains clustered into 15 heterogenic groups. (FIG. 2) Among these 15 PFGE types, P6 is the predominant type (10 strains) followed by P4 (6 strains). Additional *C. perfringens* strains may be obtained from publicly available collections.

One important factor in the identification of bacteriophage is the selection of *C. perfringens* strains suitable for their identification. In one embodiment, a method of selecting a *C. perfringens* host strain suitable to propagate bacteriophage from a plurality of test strains as a *C. perfringens* species to produce a confirmed strain; associating the confirmed strain with a poultry disease to produce a disease-associated strain; applying one or more additional selective criterion to the disease-associated strain selected from minimal antibiotic resistance and absence of animal-virulence markers other than for *C. perfringens* to produce the *C. perfringens* host strain suitable to propagate bacteriophage. In one embodiment, the selection criterion is minimal antibiotic resistance and the antibiotic resistance is tetracycline, ampicillin, tylosin, erythromycin, lincomycin, chloramphenicol or other drug resistance. The selection of strains absent from antibiotic resistance minimizes the potential transduction of plasmid or chromosomal-borne antibiotic resistance genes, into the subsequent bacteriophage cocktail. The advantage of this applied criterion, is to in advance, limit any potential resistance genes in a bacteriophage cocktail preparation. The selective criterion used for these phage cocktail host strains, are a unique extension of a unique library of *C. perfringens* strains, combined with microbiological knowledge of antibiotic resistance, along with the skills in running antibiotic susceptibility tests to ascertain the resistance profiles of the submitted host strain.

Six novel bacteriophages of the Siphoviridae or Microviridae families that infect *Clostridium perfringens* were isolated from environmental water or sewage sources. Phage were characterized, for example, at both the protein and nucleic acid level. The optimal host strain for propagation of each bacteriophage is identified and all phage are preferably negative for endogenous phage. In addition, each bacteriophage is characterized by PFGE, RAPD, SDS-PAGE, and other approaches. Stocks of all six monophages and their respective host strains are made for use in characterization and production of each phage.

The *C. perfringens*-specific monophages are capable of specifically infecting *C. perfringens* strains and are not capable of infecting/growing on *E. coli, L. monocytogenes, S. enteric* and *P. aeruginosa*. As used herein, the term *C. perfringens*-specific refers to bacteriophage and bacteriophage preparations that are capable of infecting a plurality of *C. perfringens* strains and may be capable of infecting other *Clostridium* species but are incapable of infecting at least 10 strains of *E. coli, L. monocytogenes, S. enteric* and *P. aeruginosa.*

Six bacteriophages that infect *Clostridium perfringens* were sequenced. Five of the six phages are sequenced, and each predicted open reading frame is identified in each genome. Each of the predicted genes was annotated. None of the 17 undesirable genes (Table 5.1.1) is found in the genomes of any of the five phages for which sequences were available.

Two phage cocktails, INT-401 (CPAS-7, CPAS-12, CPAS-15, CPAS-16 and CPLV-42) and INT-402 (CPAS-12, CPAS-15, CPAS-16 and CPLV-42), are prepared from five of the six monophages isolated. Both cocktails are effective in killing greater than 85% of the 46 *C. perfringens* strains screened. INT-401 was selected for use in proof-of-principle efficacy studies designed to determine the prevention of necrotic enteritis in *C. perfringens* challenged broiler chickens.

Oral Gavage of Test Article (INT-401 phage cocktail) to bird on the day of challenge (Day 14) and for the next four days significantly reduced mortality due to NE. Growth performance in this group was numerically equivalent to the non-challenged control, and appeared to be better compared to the challenged, but phage-untreated chickens. Given the fact that many chickens are naturally colonized with *C. perfringens*, the latter observation warrants further elucidation, to better examine the possible growth performance-enhancing benefits of the phage preparation.

Two of the three "in ovo" treatments had numerically reduced NE mortality (9.6 and 14.8%) when compared with the Challenged control (25.9%).

Oral Gavage of Test Article prior to challenge, or spray of Test Article to chicks at the hatchery, was ineffective in preventing NE mortality due to *C. perfringens* challenge.

The results of the studies herein suggest that *C. perfringens*-specific phage preparation can be effective in significantly reducing chicken mortality due to *C. perfringens* infections in chickens such as those causing necrotic enteritis when administered shortly after the bacterial challenge. Further dosing- and delivery-optimization studies are warranted, together with fine-tuning of the product for the optimal efficacy.

Exemplary means of administration of the bacteriophage preparations are oral administration, intramuscular injection, subcutaneous injection, intravenous injection, intraperitoneal injection, eye drop, nasal spray and the like. When the subject to be treated is a bird, the bird may be a hatched bird, including a newly hatched (i.e., about the first three days after hatch), adolescent, and adult birds. Birds may be administered the vaccine in ovo, as described in U.S. Pat. No. 4,458,630 to Sharma, for example, incorporated herein by reference.

In one embodiment, the bacteriophage preparation is administered in an animal feed such as poultry feed. The bacteriophage preparation is prepared in a number of ways. For instance, it can be prepared by simply missing the different appropriate compounds to produce the bacteriophage preparation. The resulting bacteriophage preparation can then be wither mixed directly with feed, or more conventionally impregnated onto a cereal-based carrier material such as milled wheat, maize or soya flour. Such an impregnated carrier constitutes a feed additive, for example.

The bacteriophage preparation may be mixed directly with the animal feed, or alternatively mixed with one or more other feed additives such as vitamin feed additive, a mineral feed additive, or an amino acid feed additive. The resulting feed additive including several different types of components can then be mixed in an appropriate amount with the feed. It is also possible to include the bacteriophage preparation in the animal's diet by incorporating it into a second (and different) feed or drinking water which the animal also has access to. Accordingly, it is not essential that the bacteriophage preparation is incorporated into the usual cereal-based main feed of an animal.

In one embodiment, included are the methods of identifying an optimized field delivery modes and conditions for phage cocktail applications. In one embodiment, an optimized administration condition is water administration, for up to 3 days at temperatures up to 50° C.

The bacteriophage preparation can be used for a wide variety of animals, but the use of the bacteriophage preparation is particularly preferred in domestic animals and farm livestock. Animals which may in particular benefit from the bacteriophage preparation include poultry (such as chickens, turkeys, ducks and geese), ruminants (such as cattle, horse and sheep), swine (pigs), rodents (such as rabbits) and fish. The bacteriophage preparation is particularly useful in broiler chickens.

EXAMPLES

Example 1

Characterization of *Clostridium perfringens* Isolates

Media:

Brain Heart Infusion (BHI) broth or BHI agar was used to grow all isolates. All media were obtained from EMD Chemicals, Gibbstown, N.J.

Microoganisms:

Forty-two *C. perfringens* strains were employed. One strain (Cp20) did not grow and was excluded from further analysis. As part of the collection process, isolates were checked for purity and frozen at −80° C. in 30% glycerol. Most of the work was performed in an anaerobic chamber (Plas-Labs, Lansing, Mich.), that contained a 90% $N_2$-5% $H_2$-5% $CO_2$ atmosphere.

Bacteriophage:

All bacteriophage were isolated from environmental water sources.

Phage Isolation:

Samples of water collected for the isolation of phage were mixed with 10×BHI broth, inoculated with a single *C. perfringens* strain of interest and incubated anaerobically at 37° C. overnight. The samples were centrifuged (8,000×g, 10 min) to remove the bacterial cells and sterile filtered (0.22 μm Stericup™, Millipore, Bedford, Mass.). Filtrates were serially diluted in BHI broth and tittered using soft-agar overlay method. Briefly, dilutions of each filtrate were mixed with log-phase bacterial culture, incubated 37° C. for 10 minutes, molten soft-agar added, poured onto BHI agar plates and incubated anaerobically at 37° C. overnight. Individual plaques were picked from the overlay plated and tittered a second time as an initial step in ensuring that each phage was pure.

Screening for Endogenous Phage:

*Clostridium perfringens* strains used for propagating the plaques were screened for endogenous bacteriophage by the drop lawn method. Liquid cultures of host strains were grown overnight, centrifuged (9,500×g, 5 minutes) to remove bacteria and filtered through a 0.22 μm syringe filter (Millipore). The same strains were grown in BHI broth to an $OD_{600}$ of 0.1-0.3. Two hundred microliters of each screening strain was mixed with molten soft-agar and poured onto a BHI agar plate. After the soft-agar hardened 10 μl of each host strain filtrate was spotted onto the plates with the screening strains. Lytic activity was observed after overnight anaerobic incubation at 37° C.

*Clostridium perfringens* Host Strain Typing:

The 41 *C. perfringens* strains received were typed by PFGE using the National Molecular Subtyping Network (PulseNet) standard protocol. *C. perfringens* strains were grown on BHI agar overnight anaerobically at 37° C. and suspended in 75 nM NaCl-25 mM EDTA (pH 8.0) (CSB) buffer to an $OD_{600}$ of 1.3-1.4. The bacterial cells were embedded in 1.2% SeaKem® Gold Agarose (Cambrex, Rockland, Me.) by mixing equal volumes (0.4 mL) of the cell suspension and melted agarose made in TE buffer. Plugs were made in 1.5-mm thick molds (Bio-Rad Laboratories, Hercules, Calif.) and solidified at 4° C. the cells were lysed in lysis buffer (50 mM Tris-HCl [pH 8.0], 50 mM EDTA [pH 8.0], 1% laurylsarcosine, and proteinase K [1 mg/ml]) at 55° C. overnight. The plugs were washed at 54° C. with shaking three times for 15 minutes each in sterile water and then three times in Te buffer. The plugs were stored at 4° C. in Te buffer.

Plugs were equilibrated with restriction endonuclease buffer at 25° C. overnight. The plugs were digested with SmaI (New England Biolabs, Beverly, Mass.) according to manufacturers' recommendations overnight. Restriction fragments were separated by electrophoresis through 1% agarose gel in 0.5× Tris-borate-EDTA (10×TBE, EMD Chemicals) with 1 mM thio-urea at 14° C. in a CHEF Mapper XA PFGE apparatus (Bio-Rad Laboratories) The run time was 20 hours with a voltage of 6 V/cm and a linearly ramped pulse time of 0.4 seconds to 40 seconds. The range size analyzed was 40-1,400 kilobases.

Data Handling and Analysis:

A large zone of clearing (lytic activity) produced lawns of any of the *C. perfringens* strains where culture filtrate was applied was considered positive for endogenous phage.

PFGE Results:

Forty-one strains of *C. perfringens* were isolated from various sources and characterized by pulsed-field gel electrophoresis (PFGE) typing. (Table 1) Among the 35 strains (one strain did not grow and six were not type-able due to nuclease problems) subjected to PFGE, phylogenetic analysis showed that these strains clustered into 15 heterogenic groups. (FIG. 1) Among these 15 PFGE types, P6 is the predominant type (10 strains) followed by P4 (6 strains). *C. perfringens* strain Cp 27 has accession number ATCC-8495.

| Intralytix ID | Alpharma ID | Isolation year | Source | Location | Pathogenic (yes/no) | Comment | PGFE Type |
|---|---|---|---|---|---|---|---|
| Cp1 | 7998B | 1995 | Roney | Canada | Yes | | P1 |
| Cp2 | UAZ 75 | — | — | — | — | | P2 |
| Cp3 | Wallers | 1993 | — | IL | Yes | | P3 |
| Cp4 | Pennington | 1993 | — | IL | Yes | | P4 |
| Cp5 | 96-7413 | 1996 | Roney | AL | Yes | | NT |
| Cp6 | Uaz 74 | — | — | — | — | | P5 |
| Cp7 | Warren | 1993 | — | IL | Yes | | P6 |
| Cp8 | AU1 | 1996 | — | AL | Yes | Gangrenous dermatitis | P7 |
| Cp9 | 95-949 | 1995 | Fitz-Coy | East Coast | Yes | | NT |
| Cp10 | M1 | 2000 | Fitz-Coy | East Coast | Yes | | P8 |
| Cp11 | Harmes | 1993 | — | IL | Yes | | P3 |
| Cp12 | 94-5223 | 1994 | Thayer | GA | Yes | | P6 |
| Cp13 | D00-20250 | 2000 | Fitz-Coy | MN | Yes | | NT |
| Cp14 | UDE95-1377 | 1995 | Fitz-Coy | DE | Yes | | P9 |
| Cp15 | 95-1046 | 1995 | Fitz-Coy | DE | Yes | Gall bladder | NT |
| Cp16 | F96-01993 | 1996 | Fitz-Coy | CA | Yes | | P6 |
| Cp17 | UAZ 257 | — | — | — | — | | P10 |
| Cp18 | 94-5228 | 1994 | Thayer | GA | Yes | | P11 |
| Cp19 | Gresbrecht A | 1993 | — | IL | Yes | | P6 |
| Cp20 | 96-2873 | 1996 | Roney | AL | Yes | Did not grow | * |
| Cp21 | URZ298 | — | — | — | — | | P12 |
| Cp22 | FC1 | 1995 | Fitz-Coy | East Coast | Yes | | P13 |
| Cp23 | Kendall | 1993 | — | IL | Yes | | P4 |
| Cp24 | UDE95-1372 | 1995 | Fitz-Coy | DE | Yes | | P14 |
| Cp25 | C97M3 | 1997 | — | CO | Yes | | P4 |
| Cp26 | Reed | 1993 | — | IL | Yes | | P4 |
| Cp27 | AU2 | 1996 | Roney | AL | Yes | Gangrenous dermatitis | P7 |

-continued

| Intralytix ID | Alpharma ID | Isolation year | Source | Location | Pathogenic (yes/no) | Comment | PGFE Type |
|---|---|---|---|---|---|---|---|
| Cp28 | A1A | 2002 | Skinner | DE | Yes | | P15 |
| Cp29 | 96-7414 | 1996 | Roney | AL | Yes | | P13 |
| Cp30 | 94-5230 | 1994 | Thayer | GA | Yes | | P6 |
| Cp31 | 94-5224 | 1994 | Thayer | GA | Yes | | P6 |
| Cp32 | FC2 | 1995 | Fitz-Coy | East Coast | Yes | | P4 |
| Cp33 | 94-5229 | 1994 | Thayer | GA | Yes | | P6 |
| Cp34 | 7998C | 1995 | — | Canada | Yes | | P1 |
| Cp35 | S1-1 | 2000 | Fitz-Coy | East Coast | Yes | | P6 |
| Cp36 | 94-5227 | 1994 | Thayer | GA | Yes | | P6 |
| Cp37 | Jones | 1993 | — | IL | Yes | | P6 |
| Cp38 | 6A | 2002 | Skinner | NJ | Yes | | P14 |
| Cp39 | S1-7 | 2000 | Fitz-Coy | East Coast | Yes | | NT |
| Cp40 | 7998A | 1995 | Roney | Canada | Yes | | P1 |
| Cp41 | 95-1000 | 1995 | Fitz-Coy | — | — | | P4 |
| Cp42 | AU3 | 1996 | Roney | — | — | | NT |

Figure 2:
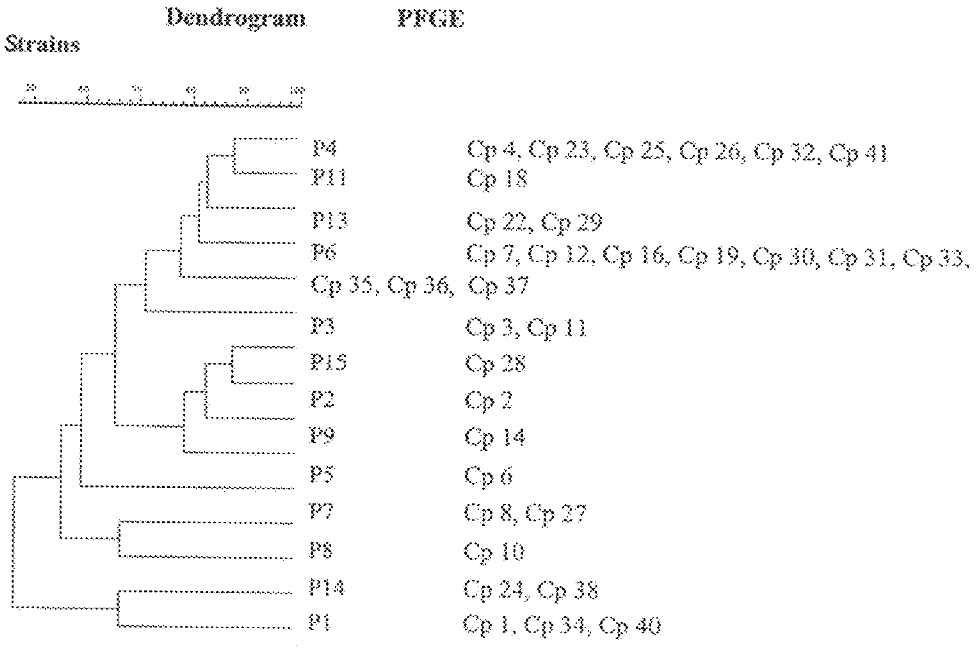
FIG. 2 is a dendrogram portraying genetic diversity of various *C. perfringens* strains based on SmaI-digested PGFE patterns of *C. perfringens* DNA.
Figure 3:
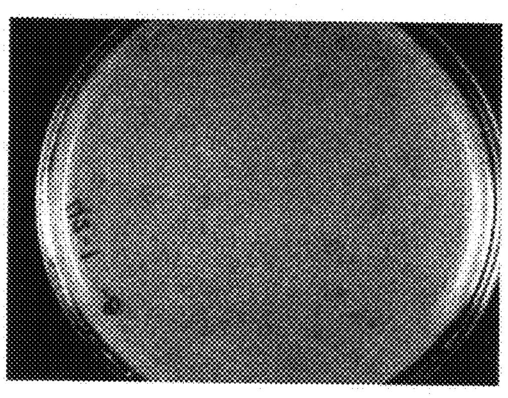
FIG. 3 shows phage plaques produced by representative bacteriophage infecting *C. perfringens* strain Cp 42.

A dendrogram portraying genetic diversity of various *C. perfringens* strains based on SmaI-digested PGFE patterns of *C. perfringens* DNA is shown in FIG. 2. Among the strains making u the 15 PFGE types, 16 strains (about 46%) were grouped into PFGE types P6 (10 strains) and P4 (6 strains). The remaining 20 strains clustered into eight PFGE types represented by a single strain (PFGE types P2, P5, P8, P9, P10, p11, p12 and p15), four PFGE type represented by two strains each (PFGE types P3, P7, P13 and P14) and one PFGE type represented by three strains (PFGE type P1). While some of the strains within the same PFGE type were associated with the same geographic location/source/year of isolation (e.g., both strains in the PFGE type P3 have come from the Illinois Disease Lab, and they both were isolated in 1995), the number of strains in the PFGE type other than P$ and P6 was too small for making generalized conclusions about their specific association with any given facility/location. Strains in the PFGE type P$ and P6 did not appear to be associated with a specific location/source of isolation (e.g., strains in the PFGE type P6 were isolated from various sources in Illinois, Georgia and California). FIG. 3 shows phage plaques produced by representative bacteriophage infecting *C. perfringens* strain Cp 42.

In sum, four to six candidate bacteriophages lytic for *C. perfringens* were isolated on phylogenetically distinct strains from environmental water sources each obtained from a different poultry farm or processing plant.

Example 2

Characterization of Phages Capable of Infecting *Clostridium perfringens*

The methods of Example 1 were also used for Example 2 where appropriate.

Phage Sterility:

Microbial contamination was determined by (1) plating 1 mL aliquots of test sample on LB agar plates and incubating replicate plates at 37° C. and 30° C. for 48 hours and (2) pre-incubating 1 mL aliquots of test sample for 37° C. for 24 hours then plating the samples on LB agar and incubating the plates for 24 hours at 37° C. One set of plates was incubated aerobically and another set anaerobically as indicated. Any bacterial growth at the indicated times denotes contamination.

Phage Purity:

Purity of phage stocks was determined by pulsed-field gel electrophoresis (PFGE) of uncut DNA. Approximately 100-200 ng of the phage DNA was electrophoresed in a 1% SeaKem Gold Agarose (Cambrex, Rockland, Me.) gel with 0.5× Sodium boric acid (1×SB: 10 mM sodium hydroxide pH adjusted to 8.5 with boric acid) buffer at 14° C. in a CHEF Mapper XA PFGE apparatus (Bio-Rad Laboratories, Hercules, Calif.). The run time is 12 hours with a voltage of 6 V/cm and a linearly ramped pulse time of 0.06 s to 8.53 seconds. The gels were stained with ethidium bromide and visualized with UV light.

Nucleic Acid Characterization:

DNA from each batch of bacteriophage was isolated by standard phenol-chloroform extraction method. Proteinase K (200 μg/ml) and RNAse A (1 μg/ml) were added to phage samples with titer≥$1\times10^9$ PFU/ml and incubated at 37° C. for 30 minutes followed by 56° C. for an additional 30 minutes. SDS/EDTA was added to a final concentration of 0.1% and 5 mM respectively and incubated at room temperature for 5 minutes. The samples were extracted once with buffered phenol, once with phenol-chloroform and once with chloroform. Phage DNA was ethanol precipitated and resuspended in 10 mM Tri-HCl (pH 8.0)-0.1 mM EDTA (TE) buffer).

Restriction maps of the phage genomes were made by digesting approximately 1 μg of the phage DNA with 10 units of XmnI (New England BioLabs, Beverly, Mass.) according to the manufacturers' recommendations. Restriction fragments were separated on 1.0% agarose gel for 16 hours at 20V in 1× Tris-acetate-EDTA (10×TAE, EMD Chemicals) buffer and bands visualized by staining with ethidium bromide.

Protein Characterization:

Phage proteins were analyzed by sodium dodecyl sulfate-polyacrylamide gel electrophoresis (SDS-PAGE). Briefly, phage samples with a titer≥$1\times10^8$ PFU/ml were denatured in a boiling water bath for minutes in NuPAGE® LDS buffer fortified with DTT (Invitrogen, Carlsbad, Calif.). Aliquots were electrophoresed in a precise NuPAGE® Novex 4 to 12% Bis-Tris continuous gradient gel (Invitrogen) at 120V for 110 minutes. Proteins were visualized on gels by silver-staining using SilverXPress® (Invitrogen) according to the manufacturers' recommendations.

*Clostridium perfringens* Phage Susceptibility:

Forty-six *C. perfringens* strains were screened for their susceptibility to the six monophages and two cocktails by the drop lawn method. Strains were streaked onto BHI agar plates and incubated at 37° C. anaerobically overnight. One colony of each strain was inoculated into separate 15-ml culture tube containing BHI broth and incubated at 37° C. anaerobically until the $OD_{600}$ reached 0.1-0.3. One hundred microliters of each strain was mixed with BHI soft-agar and poured onto a BHI agar plate. After the soft-agar hardened 10 μL of each phage was spotted in triplicate onto plates inoculated with *C. perfringens* strains. Lytic activity was observed after overnight anaerobic incubation at 37° C.

Preparation of Phage Manufacturing Batches:

Shake Flask Batches of Each phage were carried out in 2-L flasks containing 1.5 L of BHI broth. *Clostridium perfringens* strains were grown in BHI broth anaerobically overnight at 37° C., subcultured and grown to an $OD_{600}$ of 0.1-0.3. Cultures were infected at an MOI previously determined to be optimal for each phage (See Table 5.1.4). Growth was monitored spectrophotometrically until lysis occurred and phage harvested by vacuum filtration (SteriCup, Millipore). Batches of each phage were concentrated separately and buffer exchanged with PBS by tangential flow filtration in a Pellicon® Mini Cassette using a 50 kDa filter (Millipore).

Endotoxin Levels:

Endotoxin levels for lots of phage produced were determined by a *Limulus* amoebocyte lysate (LAL) assay using a chromogenic assay (QCL-1000 Kit, BioWhittaker, Walkersville, Md.) following manufacturers' recommendations. A standard curve with *E. coli* endotoxin (supplied with kit) ranging from 0.1 to 1.0 endotoxin units (EU) per milliliter endotoxin is constructed for each assay by plotting the optical density at 405 nm ($OD_{405}$) versus EU/ml. Phage samples are assayed diluted in sterile water (USP, Baxter, Deerfield, Ill.) and the absorbance at 405 nm was measured with a μQuant (Bio-Tek Instruments, Inc., Winooski, Vt.) microplate reader.

Endotoxin concentrations for each sample are calculated by linear regression from the standard curve. Standards and samples are analyzed in triplicate.

Carbohydrate Content:

Carbohydrate content for all lots of phage produced is determine by an anthrone method. A standard curve with glucose ranging from 10 to 250 μg/ml is constructed for each assay by plotting optical density at 625 nm ($OD_{625}$) versus μg/ml glucose concentration. Phage samples are assayed in PBS and the absorbance at 625 nm was measured with a μQuant (Bio-Tek Instruments, Inc., Winooski, Vt.) microplate reader.

Carbohydrate concentrations for each sample are calculated by linear regression from the standard curve. Standards and samples are analyzed in triplicate.

Total Protein Content:

The total protein content for all lots of phage produced is determine by a bicinchoninic acid (BCA) assay using a colorometric assay (BCA™ Protein Assay kit, Pierce, Rockford, Ill.) following manufacturers' recommendations. A standard curve with bovine serum albumin ranging from 20 to 2000 μg/ml protein is constructed for each assay by plotting optical density at 562 nm ($OD_{562}$) versus μg/ml BSA. The absorbance at 562 nm was measured with a μQuant (Bio-Tek Instruments) microplate reader.

Total protein concentrations for each sample are calculated by linear regression from the standard curve. Standards and samples are analyzed in triplicate.

Electron Microscopy:

High-titer phage lysates (≥$10^8$ PFU/ml) were centrifuged at 31,000×g for 2 hours and resuspended in 100 mM ammonium acetate (pH 7.0). A drop of phage suspension was deposited on a carbon-coated Fromvar copper grid of 400 mesh. The phages were negatively stained by adding a drop of potassium phosphotungstate (102% pH 7) and after one minute the excess fluid was withdrawn. Pictures of the phage particles were taken with a Phillips EM 300 transmission electron microscope at an acceleration voltage of 60 kV with a primary magnification of 29,700×.

Results:

Six novel bacteriophages that infect *Clostridium perfringens* were isolated from environmental water or sewage sources. Each phage was characterized at both the protein and nucleic acid level. The optimal host strain for propagation of each bacteriophage was identified and all were negative for endogenous phage (Table 2).

TABLE 2

Optimal *C. perfringens* host strains for propagating *C. perfringens*-specific phages.

| Phage | Host |
|---|---|
| CPLV-42 | Cp27 |
| CPAS-7 | Cp8 |
| CPAS-12 | Cp26 |
| CPTA-37 | Cp27 |
| CPAS-15 | Cp8 |
| CPAS-16 | Cp42 |

Stocks of all six monophages and their respective host strains were made for use in characterization and production of each phage.

Figure 4:
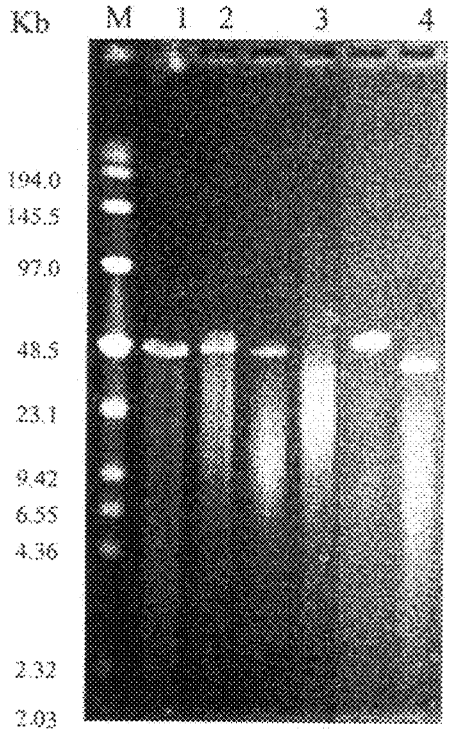
FIG. 4: Pulsed-field gel electrophoresis analysis of undigested phage DNA isolated from each monophage. Lane M, Low Range PFG Marker (NEB); lane 1, CPAS-7; lane 2 CPAS-15, lane 3, CPAS-16; lane 4, CPLV-42; lane 5 CPTA-12; lane 6, CPAS-37.
Figure 5:
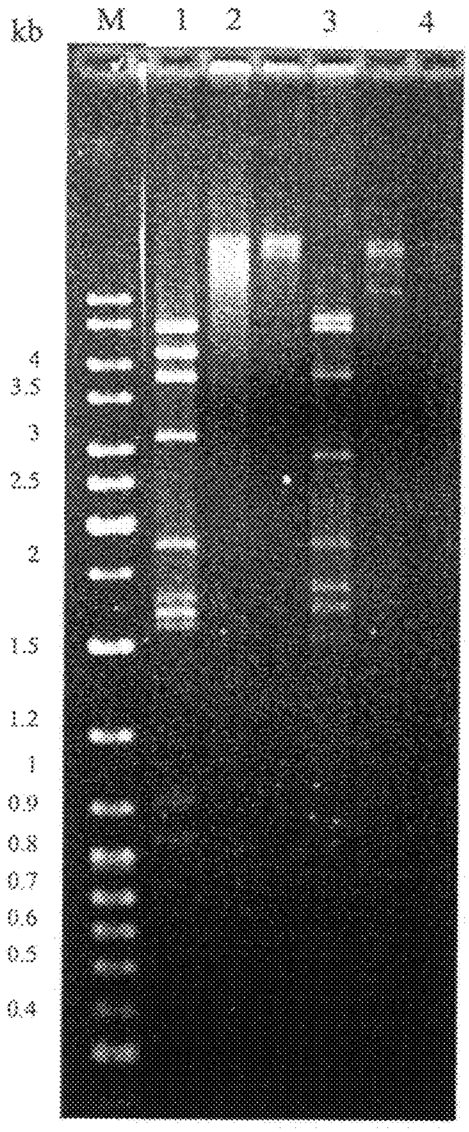
FIG. 5 shows XmnI digested phage DNA from each monophage. Lane M, GeneRuler DNA Ladder Mix (Fermentas); lane 1, CPLV-42; lane 2, CPAS-7, lane 3, CPAS-15; lane 4, CPTA-37; lane 5 CPAS-12; lane 6, CPAS-16.
Figure 6:
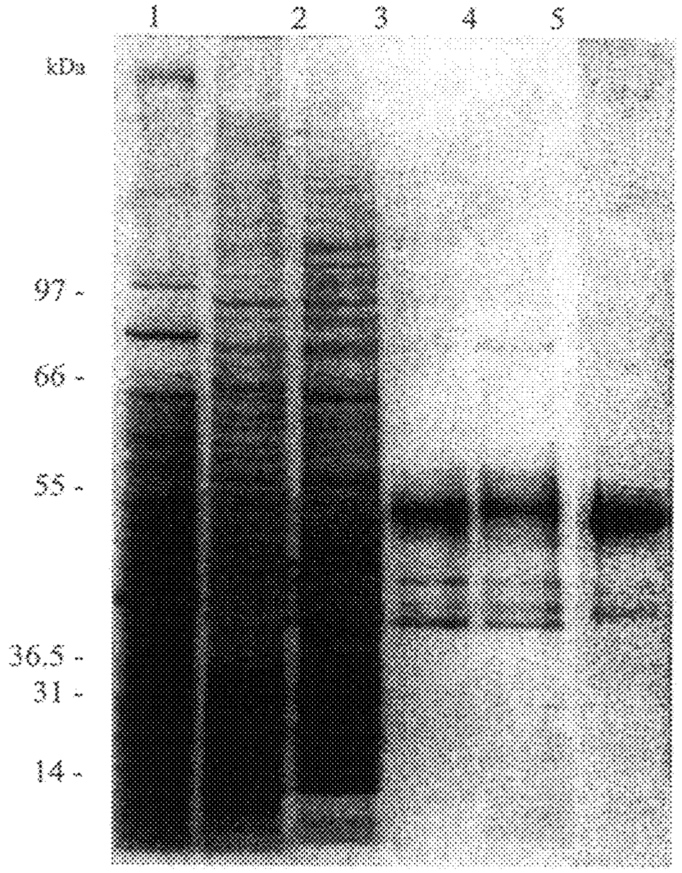
FIG. 6 shows structural protein profiles for each *C. perfringens* monophage. Lane 1, CPLV-42; lane 2, CPAS-12, lane 3, CPAS-7; lane 4, CPAS-16; lane 5 CPAS-15; lane 6, CPTA-37.

PFGE analysis of uncut DNA from each of the isolated phages showed that they were pure monophages with genome sizes of 36 to 50 kb (FIG. 4). DNA from each monphage isolated was digestible with XmnI (FIG. 5). All six of the monophages showed different protein profiled on SDS_PAGE or RFLP profiles confirming that all six monophages are different from one another (FIG. 6).

Figure 7:
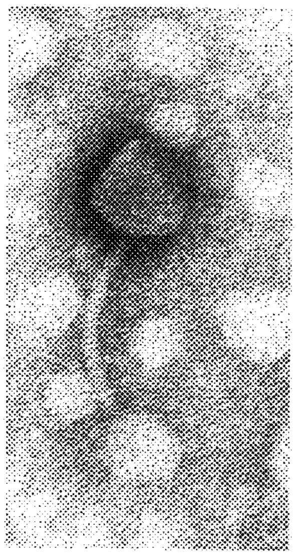
FIG. 7 shows electron micrographs of *C. perfringens* bacteriophages.
Figure 7:
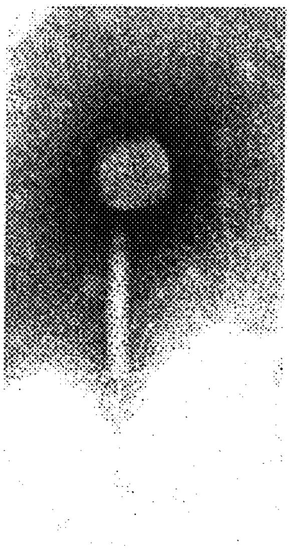
Figure 7:
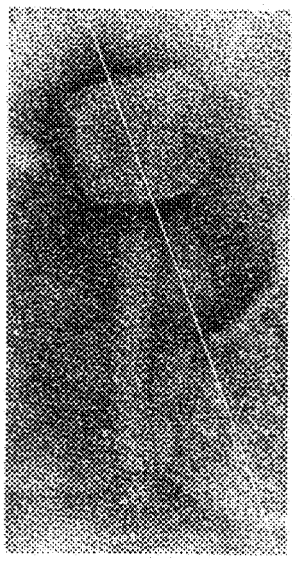
Figure 7:
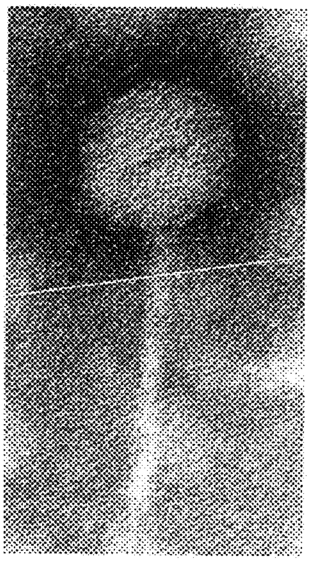
Figure 7:
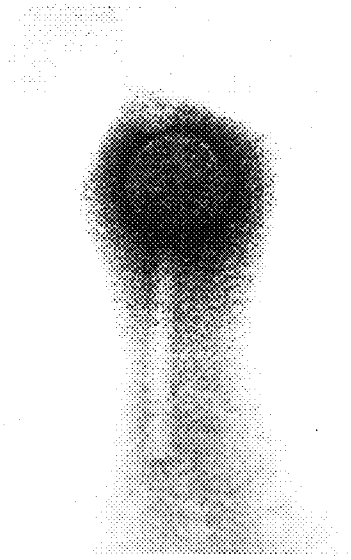

Electron microscopy showed the bacteriophages to be members of the Siphoviridae or Myoviridae families of icosahedral head phages (FIG. 7) with long tails and double-stranded DNA genomes.

The ability of the six *C. perfringens* monophages to infect 46 *C. perfringens* strains is shown in Table 3. Phage CPLV-42, CPAS-16, CPTA-37, CPAS-7, CPAS-12 and CPAS-15 infected 20%, 87%, 13%, 39%, 74% and 52% of the strains screened respectively. The specificity of the phages for *C. perfringens* was examined by screening the susceptibility of ten stains of *E. coli, L. monocytogenes, S. enteric* and *P. aeruginosa*. None of these 40 strains were infected by any of the monophages isolated against *C. perfringens* (Table 4).

TABLE 3

Susceptibility of *C. perfringens* strains to *C. perfringens*-specific bacteriophage

| | Phage | | | | | | Cocktail | |
|---|---|---|---|---|---|---|---|---|
| Strain | CPLV-42 | CPAS-16 | CPAS-12 | CPAS-15 | CPAS-7 | CPTA-37 | INT-401 | INT-402 |
| ATCC 13124 | + | + | + | + | + | − | + | + |
| Cp1 | − | + | − | − | − | − | + | + |
| Cp2 | − | − | + | + | + | − | + | + |

TABLE 3-continued

Susceptibility of *C. perfringens* strains to *C. perfringens*-specific bacteriophage

| Strain | Phage | | | | | | Cocktail | |
|---|---|---|---|---|---|---|---|---|
| | CPLV-42 | CPAS-16 | CPAS-12 | CPAS-15 | CPAS-7 | CPTA-37 | INT-401 | INT-402 |
| Cp3 | − | + | + | − | − | − | + | + |
| Cp4 | − | + | + | + | − | − | + | + |
| Cp5 | − | + | + | + | − | − | + | + |
| Cp6 | − | + | + | − | − | − | + | + |
| Cp7 | + | + | + | + | + | − | + | + |
| Cp8 | + | + | − | + | + | − | + | + |
| Cp9 | − | + | + | + | − | − | + | + |
| Cp10 | − | + | − | + | − | − | + | + |
| Cp11 | − | + | + | − | − | − | + | + |
| Cp12 | − | + | + | − | − | − | + | + |
| Cp13 | − | + | + | + | − | − | + | + |
| Cp14 | − | + | − | + | + | − | + | + |
| Cp15 | + | + | + | − | − | − | + | + |
| Cp16 | − | + | + | + | + | − | + | + |
| Cp17 | − | + | + | + | + | − | + | + |
| Cp19 | − | + | + | − | − | − | + | + |
| Cp21 | − | + | + | − | − | − | + | + |
| Cp22 | + | + | + | + | − | − | + | + |
| Cp23 | − | + | + | + | + | − | + | + |
| Cp24 | − | + | + | + | − | − | + | + |
| Cp25 | − | + | + | + | + | − | + | + |
| Cp26 | − | + | + | − | − | − | + | + |
| Cp27 | + | + | + | − | − | + | + | + |
| Cp28 | − | + | − | − | − | − | + | + |
| Cp29 | − | + | − | − | + | − | + | − |
| Cp30 | − | + | + | − | − | − | + | + |
| Cp31 | − | − | + | − | − | − | + | − |
| Cp32 | + | + | − | + | + | + | + | − |
| Cp33 | − | + | + | + | − | − | + | − |
| Cp34 | − | − | − | + | + | + | + | + |
| Cp35 | − | + | − | + | + | − | + | + |
| Cp36 | − | − | + | + | − | − | + | + |
| Cp37 | − | + | + | − | − | − | + | + |
| Cp38 | − | + | + | + | + | − | + | + |
| Cp39 | − | + | − | − | − | − | + | + |
| Cp40 | − | + | − | − | − | − | + | + |
| Cp41 | − | − | + | − | + | + | + | + |
| Cp42 | + | + | + | + | + | + | + | + |
| Cp43 | − | + | + | − | − | − | + | + |
| Cp44 | − | + | + | − | + | − | + | + |
| Cp45 | − | + | + | − | − | − | + | + |
| Cp46 | − | − | − | − | − | − | − | − |
| Cp47 | + | + | + | + | + | + | + | + |

TABLE 4

Susceptibility of other bacterial strains to *C. perfringens*-specific bacteriophage

| Strain | Phage | | | | | |
|---|---|---|---|---|---|---|
| | CPLV-42 | CPAS-16 | CPAS-12 | CPAS-15 | CPAS-7 | CPTA-37 |
| *Pseudomonas aeruginosa* | | | | − | − | − |
| Pa1 | − | − | − | − | − | − |
| Pa3 | − | − | − | − | − | − |
| Pa7 | − | − | − | − | − | − |
| Pa15 | − | − | − | − | − | − |
| Pa21 | − | − | − | − | − | − |
| Pa33 | − | − | − | − | − | − |
| Pa42 | − | − | − | − | − | − |
| Pa62 | − | − | − | − | − | − |
| Pa65 | − | − | − | − | − | − |
| Pa72 | − | − | − | − | − | − |
| *Salmonella enterica* | | | | | | |
| SE24 | − | − | − | − | − | − |
| SS28 | − | − | − | − | − | − |
| ST31 | − | − | − | − | − | − |
| SHE43 | − | − | − | − | − | − |
| SH49 | − | − | − | − | − | − |
| S45 | − | − | − | − | − | − |

TABLE 4-continued

Susceptibility of other bacterial strains to *C. perfringens*-specific bacteriophage

| | Phage | | | | | |
|---|---|---|---|---|---|---|
| Strain | CPLV-42 | CPAS-16 | CPAS-12 | CPAS-15 | CPAS-7 | CPTA-37 |
| S AE 72 | – | – | – | – | – | – |
| SK 103 | – | – | – | – | – | – |
| SR114 | – | – | – | – | – | – |
| SH162 | – | – | – | – | – | – |
| *Listeria monocytogenes* | | | | | | |
| Lm6 | – | – | – | – | – | – |
| Lm10 | – | – | – | – | – | – |
| Lm23 | – | – | – | – | – | – |
| Lm31 | – | – | – | – | – | – |
| Lm35 | – | – | – | – | – | – |
| Lm49 | – | – | – | – | – | – |
| Lm62 | – | – | – | – | – | – |
| Lm67 | – | – | – | – | – | – |
| Lm79 | – | – | – | – | – | – |
| Lm86 | – | – | – | – | – | – |
| *Escherichia coli* | | | | | | |
| Ec3 | – | – | – | – | – | – |
| Ec26 | – | – | – | – | – | – |
| Ec37 | – | – | – | – | – | – |
| Ec41 | – | – | – | – | – | – |
| Ec56 | – | – | – | – | – | – |
| Ec60 | – | – | – | – | – | – |
| Ec65 | – | – | – | – | – | – |
| Ec68 | – | – | – | – | – | – |
| Ec73 | – | – | – | – | – | – |
| Ec77 | – | – | – | – | – | – |

The following strains were used to demonstrate the overall activity of the phage cocktail INT-401, versus a standard set of *Clostridium perfringens* strains available from depositories. Strains were evaluated for lysis by spotting 10 microliters containing $10^8$ pfu/ml onto pure lawns of each test strain spread onto BHI agar, and incubating overnight at 37° C.

TABLE 5

| Depository | Strain Identifier Number | INT-401 Lysis |
|---|---|---|
| ATCC | 25768 | + |
| ATCC | 3624 | + |
| ATCC | 9856 | + |
| ATCC | 3628 | + |
| ATCC | 13124 | + |
| ATCC | PTA-50143 | + |
| NRRL | B-50143 (CP8) | + |
| NRRL | B-50144 (CP26) | + |
| NRRL | B-50145 (CP42) | + |

6 monophages were then isolated. (Table 6) Two phage cocktails INT-401 (CPAS-7, CPAS-12, CPAS-15, CPAS-16 and CPLV-42) and INT-402 (CPAS-12, CPAS-15, CPAS-16 and CPLV-42), were prepared from five of the six monophages isolated. Table 7 gives the levels of endotoxin, total carbohydrate, and total protein in *C. perfringens*-specific cocktails. Both cocktails were effective in killing greater than 85% of the 46 *C. perfringens* strains screened. INT-401 was selected for use in proof-of-principle efficacy studies designed to determine the prevention of necrotic enteritis in *C. perfringens* challenged broiler chickens. This cocktail contains the five bacteriophages with the broadest host range and is likely to provide a broader (compared to INT-402) spectrum of activity in actual use against wild-type *C. perfringens* strains.

TABLE 6

Summary of *C. perfringens* monphage batch preparation

| Phage | Host Strain | MOI | Culture Time (h) | Titer (PFU/ml) |
|---|---|---|---|---|
| CPLV-42 | Cp27 | 1 | 5 | $5 \times 10^{10}$ |
| CPAS-16 | Cp42 | 1 | 3 | $1 \times 10^8$ |
| CPAS-12 | Cp26 | 1 | 4-5 | 1 × 108 |
| CPTA-37 | Cp27 | 1 | 4.5 | $4 \times 10^8$ |
| CPAS-15 | Cp8 | 1 | 4-5 | $5 \times 10^8$ |
| CPAS-15 | Cp8 | 1 | 4-5 | $6 \times 10^9$ |

TABLE 7

Levels of endotoxin, total carbohydrate, and total protein in *C. perfringens*-specific cocktails.

| Content | INT-401 | INT-402 |
|---|---|---|
| Endotoxin (EU/ml) | 384 | 288 |
| Total Carbohydrate (μg/ml) | 170 | 43 |
| Total protein (μg/ml) | 661 | 175 |

Example 3

Protocol for Bacteriophage Treatment as Therapy or Prevention of Necrotic Enteritis in Broiler Chickens Challenged with *Clostridium perfringens*

Broiler Chickens:

A total of 576 male day-old broiler chickens were assigned to treatment on day 0. There were no vaccinations (Mareks or Bronchitis) or antibiotics applied to eggs or chicks at the hatchery.

Housing:

The 64-pen broiler chicken research facility at maple leaf Agresearch was used to conduct the study. Forty-eight pens, each providing approximately 10 square feet of floor space, were assigned to treatment groups. Each pen had a concrete floor and nylon mesh partitions supported by PVC frame. Adjacent pens were separated by a solid 12-inch high plastic barrier at bird level. Each pen was permanently identified by number and contained 12 birds on day 0. The barn was heated by two natural gas heaters, which were equally spaced and positioned to warm incoming air at the south wall of the building. Air was exhausted by fans located on the north-facing wall of the building. Each pen contained one nipple-type drinker, which provided clean drinking water ad libitum. Water was de-chlorinated. Dry feed was provided ad libitum in trough-type feeders (one per pen) of 5-kg capacity. New wood shavings were used as bedding.

Management:

Lighting program, barn temperature, litter type and other management practices were typical of commercial broiler chickens producers in the local geographic area and is fully documented in the raw data. Birds, which were moribund and unable to reach food or water, were culled and euthanized by carbon dioxide gas.

Bodyweight, pen number, date of death and cause of death were determined by necropsy and recorded for each bird culled or found dead during the study.

Experimental Design:

A randomized complete block design was used to study the effects of eight treatments. The treatments were as follows:

TABLE 8

Treatment design

| Treatment code | *C. perfringens* challenge | Test Article |
|---|---|---|
| 1 | No | No |
| 2 | Yes | No |
| 3 | Yes | Yes |
| 4 | Yes | Yes |
| 5 | Yes | Yes |
| 6 | Yes | Yes |
| 7 | Yes | Yes |
| 8 | Yes | Yes |

There were 8 pens per block (8 treatments) and 6 blocks (replicates) for a total of 48 pens. (See Section 4.2, Deviation #2 for change to above treatment to block assignment).

Treatment Groups:

Treatment 1—Control UUC (no *C. perfringens* challenge or bacteriophage administration)

Treatment 2—Control IUC (*C. perfringens* challenge or without bacteriophage cocktail)

Treatment 3—In ovo injection of phage cocktail at day 18 incubation.

Treatment 4—Spray application of phage cocktail to chicks after hatching.

Treatment 5—In ovo injection of phage cocktail at day 18 incubation and spray application of phage cocktail to chicks after hatching.

Treatment 6—In ovo injection of phage cocktail at day 18 incubation, spray application of phage cocktail to chicks after hatching and oral gavage of bacteriophage cocktail on Day 7 through 13.

Treatment 7—Bacteriophage cocktail administered via oral gavage from Day 7 through 13 (oral gavage ceased on the day of *Clostridium perfringens* challenge).

Treatment 8—Bacteriophage cocktail administered via oral gavage beginning on Day 14 (concurrent with *Clostridium perfringens* challenge) through Day 18.

Feeding Program:

The following feeding program was used in the study:

TABLE 9

Feeding Program

| Day | Feed Type | Formulation Number |
|---|---|---|
| 0-13 | | |
| 9:00 p.m. Day 13 to 9:00 a.m. Day 14 | Starter | 282 |
| 14-21 | None. Feed was withdrawn | None |
| | Starter | 282 |

Feed Sampling:

The investigator's representative was present during feed manufacture. Ten representative samples were taken from each batch of final feed, composited and divided into three samples for proximate analysis, and retainer samples, respectively.

Administration of *Clostridium perfringens* Challenge:

A *Clostridium perfringens* isolate originating from a field case of necrotic enteritis in Ontario was used in the study. Inoculums contained approximately $10^8$ cfu *Clostridium perfringens* per mL at time of feeding. Feed was withdrawn from all birds for approximately 8 hours prior to first introduction of challenge. Inoculum was administered to birds via feed in the afternoon and night commencing Day 14 P.M. and ending Day 15 A.M. using trough-type feeders. A suitable quantity of assigned feed (approximately 0.150 kg) and an amount of inoculum equal to approximately 1.5 times the weight of feed was added to each feeder. When this procedure was complete for all pens assigned to the challenge, feeders were returned to their corresponding pen. Inoculum-feed mixture remaining at the end of the half-day period was weighed and discarded.

Lesion Scoring of Sacrificed Birds:

Three birds were randomly selected from each pen on Day 16 and euthanized. These birds were scored grossly for necrotic enteritis and coccidiosis lesions:

TABLE 10

Necrotic enteritis scoring

| Necrotic enteritis score | Description |
|---|---|
| 0 | Normal, no evidence of gross lesions |
| 1 | Thin, friable small intestine |
| 2 | Focal necrosis and/or ulceration |
| 3 | Patchy necrosis |
| 4 | Severe extensive necrosis (typically seen in birds which have died from NE) |

*Clostridium perfringens* Culture of Small Intestine Segment:

A small intestinal segment was collected from 40 birds that died on or after Day 15 and had a gross diagnosis of necrotic enteritis. The segment was forwarded to the Department of Pathology at the University of Guelph for *C. perfringens* culture. Culture results were reported as positive or negative for *C. perfringens*. Samples of positive bacterial cultures were forwarded to Intralytix for testing for phage susceptibility. In addition, 144 ileum samples were collected from birds sacrificed for *C. perfringens* lesion scoring on Day 16. These samples were quantitatively tested at the above referenced laboratory and microbiological samples were forwarded to Intralytix for additional characterization of phage activity.

Necropsy:

All birds that died or were euthanized were submitted to the study pathologist for gross necropsy to determine the cause of death.

Observation and calculation of variables:

1) Bodyweight and number of birds per pen on Days 0, 14, and 21.
2) Amounts of each feed consumed by each pen.
3) Bodyweight and date of death for birds which were culled or died
4) Feed conversion was calculated on a pen basis as feed consumed/[total weight of live birds+total weight of dead and culled birds+total weight of sacrificed birds] for the 0-14, 14-21 and 0-21 Day periods.
5) Average bodyweight per pen was calculated as a total weight of live birds at the time of weighing/number of live birds at the time of weighing.
6) Daily feed intake (grams) per live bird day was calculated on a pen basis for Day-14, Day 14-21 and Day 0-21.
7) Apparent cause of death was recorded for all birds that died or were culled. Total mortality and mortality from necrotic enteritis will be calculated on a pen basis.
8) Evaluation of the effects of the in ovo injection treatments on percent hatch and chick health at the hatchery
9) Necrotic enteritis lesion score of sacrificed birds (Day 16).
10) Birds were observed on a flock basis at least once daily and observations were recorded.

Test Substance Disposition:

Remaining bacteriophage cocktail test substance was destroyed by incineration and destruction is documented in the study records.

Bird Disposition:

Birds (treated and control) were humanely euthanized at the end of the study and disposed of via incineration and method and date of disposition was recorded in the study records. Hatchery waste and unused in ovo bacteriophage injected eggs were disposed of via incineration. Hatched chicks that had been in ovo injected or sprayed with bacteriophage but not assigned to the study were humanely euthanized and disposed of via incineration.

Original Data:

Original data is submitted to the sponsor together with the final report. An exact copy of the final report and data will be maintained at Maple Leaf Agresearch for a minimum of two years.

Documentation:

All raw (original) data was recorded in black ink on data sheets bearing the trial number. Corrections were made by drawing a single line through the original entry and writing the correct entry beside it together with initials of the person making the correction, the date the correction was made and the reason for the correction. Defined error codes were used to record the reason for correcting a data point.

Statistical Analysis:

Randomized complete block design was to be used. Pen location within the facility was the blocking factor. The pen was the experimental unit for statistical analysis. A one-way treatment structure was utilized with each treatment being replicated six times (once within each block, except as detailed in Deviation #2, Section 4.2). Mortality data was transformed prior to analysis of variance. Mixed models analysis was used to analyze all data. Means were compared using an appropriate multiple range test.

Amendment #1:

This amendment clarifies dates, eliminated vaccine administration and any potential interference vaccine might have with the Test Article, and detailed exact doses of Test article to be administered during "in ova" injection (0.2 mL), spraying (about 7 mL per 100 chicks) and oral dosing (0.5 mL per bird per day).

Amendment #2:

This amendment redefined the dosage of "in ovo" administration (0.05 mL per egg), spraying (about 7 to 22 mL per 100 chicks). The upper range of 22 mL was actually used for the spray.

Deviations:

Two deviations occurred and are described in the Protocol section of the Study Binder. A brief description follows:

Deviation #1:

Only 12 birds were assigned to pens instead of 15 described in the protocol. This will have an impact on the statistical power of the study, particularly the mortality data.

Deviation #2:

Block 3 was assigned 2 treatment pens and no treatment 5 pen caused an imbalance in the design. Least square means will be reported to correct for the unequal representation per treatment group. This is not expected to have a major influence on the power of the study.

Example 4

Results for Bacteriophage Treatment as Therapy or Prevention of Necrotic Enteritis in Broiler Chickens Challenged with *Clostridium perfringens*

The results of this study are summarized in Tables 10 to 12. A detailed statistical analysis was performed.

Hatchery: "in ovo" injection of eggs with test Article (0.05 mL per egg) for Treatments 3, 5 and 6 was performed at 18 days of incubation using an Embrex machine and followed the standard industry protocol with the following exceptions: Marek's vaccine and antibiotic (Excenel) were not included. The standard procedure also involved applying a small amount of chlorine solution over the injection hole just post injection. For this trial, 1259 fertile eggs were transferred without being injected and hatched at 96.6%. The 775 fertile eggs injected with Test Article hatched at 95.5%.

TABLE 11

Delivery Routes of Bacteriophage on weights of broiler chickens challenged with necrotic enteritis.

| | Average live weights (kg)[2] | | | | |
|---|---|---|---|---|---|
| Treatment[1] | Day 0 | Day 14 | Day 21 | Day 35 | Day 42 |
| Control | .046 | .330 | .750$^{A}$ | 1.917$^{A}$ | 2.776$^{A}$ |
| Challenged control | .046 | .340 | .618$^{C}$ | 1.530$^{C}$ | 2.342$^{C}$ |
| BMD control | .045 | .340 | .634$^{C}$ | 1.795$^{B}$ | 2.686$^{AB}$ |

TABLE 11-continued

Delivery Routes of Bacteriophage on weights of broiler chickens challenged with necrotic enteritis.

| Treatment[1] | Average live weights (kg)[2] | | | | |
|---|---|---|---|---|---|
| | Day 0 | Day 14 | Day 21 | Day 35 | Day 42 |
| Gavaged phage | .045 | .328 | .641$^{C}$ | 1.762$^{B}$ | 2.601$^{B}$ |
| Phage in water | .046 | .348 | .694$^{B}$ | 1.812$^{AB}$ | 2.664$^{AB}$ |
| Phage in feed | .045 | .333 | .658$^{BC}$ | 1.754$^{B}$ | 2.592$^{B}$ |
| SEM | .000 | .010 | .018 | .045 | .059 |
| Pr > F | .5309 | .7492 | .0003 | .0001 | .0004 |

[1]LSMEANS were provided for each treatment. The treatment group included a control. Challenged control, BMD 50 g/ton as a medicated control, oral gavaged phage, phage provided via water and phage provided via feed. The bacteriophage used was Intralytix *C. perfringens* Phage Cocktail - 4.8 × $10^9$ pfu/ml. On Day 14, all the birds were orally inoculated with a coccidial inoculums containing approximately 5,000 oocysts of *E. maxima* per bird. All groups were challenged with *Clostridium perfringens* on Days 18, 19, and 20. Oral Administration of phage cocktail via gavage drinking water and feed application will occurred on days 17, 18, 19, 20, and 21.

[2]Standard error of the LSMEANS

[A,B,C]Means within columns with different subscripts are significantly different.

Three treatments (#'s 4, 5 and 6, Table 10) were also sprayed with Test Article at the hatchery after hatch. A commercial spray cabinet designed for administering coccidiosis vaccine was used to deliver the Test Article at a rate of 22 mL per box or approximately 0.22 mL per bird. These birds were held in the hatchery for an extra ½ hour to permit drying to transport to the research farm.

Challenged pens were provided with 1.66 kg of *Clostridium perfringens* inoculums/feed mixture and all consumed at least 1.25 kg except one, a challenged control pen. This pen suffered from severe water restriction due to a technical problem and for this reason was removed from the analysis. Due to the deviation described above the challenged control (Treatment 2) was assigned one extra pen and Treatment 5 one less pen. With this slight imbalance in design, least squares means are reported. There was no significant (p>0.05) difference between challenged groups in quantity of inoculum consumed.

The primary criteria for evaluating the effectiveness of Test Article and its method of administration is mortality attributable directly to *Clostridium perfringens* challenge. No birds died from Necrotic Enteritis (NE) in the non-challenged control (Treatment 1) and this was significantly (p<0.01) different than the challenged control with 25.9% of the birds in a pen dying of NE. Birds treated (Treatment 8) by Oral Gavage (OG) from the day of challenge (day 14) until day 18 had the lowest mortality (5.6%) of the phage treated groups and this was not significantly (p>0.05) different from the non-challenged control (Treatment 1). Two of the "in ovo" groups (Treatment 3 and 6) had intermediate NE mortality, which was not significantly (p>0.05) different from either Control groups (Treatments 1 and 2).

Three birds per pen were sacrificed at Day 16 to detect lesions typical of NE and to determine the presence of *Clostridium perfringens* in either a defined segment (approximately 3 to 4 cm distal to the duodenum) if not lesions were present or a segment surrounding an identified lesion. Although not significantly (p>0.05) different from the other treatment groups, there were no "typical" NE lesions found in the non-challenged control (Treatment 1). No significant (p>0.05) difference between treatments was found for lesion scores. *Clostridium perfringens* (Cp) bacterium were isolated from all groups including the non-challenged control. We do not know if the strain isolated from the non-challenged control was the same as the challenged strain. However, Treatment 1 was numerically lower for Bacterial Scores for Cultures and this was consistent with the significantly (p<0.05) lower scores (Table 1) for Smears. No other trends were evident in the Bacterial Score means for either Cultures or Smears between the other treatment groups.

TABLE 12

Delivery Routes of Bacteriophage on weight gains of broiler chickens challenged with necrotic enteritis

| Treatment[1] | Average live weights (kg)[2] | | | | |
|---|---|---|---|---|---|
| | Day 0-14 | Day 0-21 | Day 14-21 | Day 0-35 | Day 0-42 |
| Control | .284 | .705$^{A}$ | .421$^{A}$ | 1.871$^{A}$ | 2.730$^{A}$ |
| Challenged control | .294 | .572$^{C}$ | .278$^{C}$ | 1.484$^{C}$ | 2.296$^{C}$ |
| BMD control | .295 | .589$^{C}$ | .294$^{C}$ | 1.750$^{B}$ | 2.641$^{AB}$ |
| Gavaged phage | 283 | .596$^{C}$ | .313$^{BC}$ | 1.716$^{B}$ | 2.556$^{B}$ |
| Phage in water | .302 | .648$^{B}$ | .346$^{B}$ | 1.766$^{AB}$ | 2.618$^{AB}$ |
| Phage in feed | .287 | .612$^{BC}$ | .325$^{BC}$ | 1.709$^{B}$ | 2.547$^{B}$ |
| SEM | .010 | .018 | .014 | .045 | .059 |
| Pr > F | .7559 | .0003 | .0001 | .0001 | .0004 |

[1]LSMEANS were provided for each treatment. The treatment group included a control. Challenged control, BMD 50 g/ton as a medicated control, oral gavaged phage, phage provided via water and phage provided via feed. The bacteriophage used was Intralytix *C. perfringens* Phage Cocktail - 4.8 × $10^9$ pfu/ml. On Day 14, all the birds were orally inoculated with a coccidial inoculums containing approximately 5,000 oocysts of *E. maxima* per bird. All groups were challenged with *Clostridium perfringens* on Days 18, 19, and 20. Oral Administration of phage cocktail via gavage drinking water and feed application will occurred on days 17, 18, 19, 20, and 21.

[2]Standard error of the LSMEANS

[A,B,C]Means within columns with different subscripts are significantly different.

There was a significant (p<0.05) higher chick weight for one of the groups (Treatment 4) receiving Test Article by Spray at the hatchery. This was not significantly different than one (Treatment 5) of the other two groups receiving the Spray. This may be the result of these Treatments retaining more moisture from the Spray procedure. Pre-challenge, on Day 14, there were no significant differences (p>0.05) in body weight between Treatments. After challenge, at Day 21, the non-challenged control (Treatment 1) was significantly (p<0.05) heavier than the birds receiving Test Article by Oral Gavage (Treatment 7) prior to challenge. No other differences in growth performance were detected.

Total mortality in the non-challenged control was high at 13.9%. As indicated in the necropsy records much of this non-NE mortality was due to internal infections, omphalitis (yolk sac infections) and sudden death. This high early chick mortality is not typical. Total mortality was significant (p<0.05) lower for the non-challenged control (Treatment 1, 13.9%) and the birds receiving Oral Gavage from day 14 to day 18 (Treatment 8, 12.5%) than Treatment 5 (37.0%).

TABLE 13

Delivery Routes of Bacteriophage on feed conversion of broiler chickens challenged with necrotic enteritis

| Treatment[1] | Feed conversion ratio (feed to gain) | | | | |
|---|---|---|---|---|---|
| | Day 0-14 | Day 0-21 | Day 14-21 | Day 0-35 | Day 0-42 |
| Control | 1.703 | 1.532$^{D}$ | 1.417$^{C}$ | 1.709$^{D}$ | 1.892$^{D}$ |
| Challenged control | 1.600 | 1.912$^{A}$ | 2.284$^{A}$ | 2.483$^{A}$ | 3.226$^{A}$ |
| BMD control | 1.561 | 1.892$^{AB}$ | 2.130$^{A}$ | 2.077$^{B}$ | 2.652$^{B}$ |
| Gavaged phage | 1.662 | 1.760$^{BC}$ | 1.864$^{B}$ | 1.814$^{CD}$ | 2.086$^{C}$ |
| Phage in water | 1.562 | 1.676$^{C}$ | 1.778$^{B}$ | 1.813$^{CD}$ | 2.066$^{C}$ |

TABLE 13-continued

Delivery Routes of Bacteriophage on feed conversion of broiler chickens challenged with necrotic enteritis

| Treatment[1] | Feed conversion ratio (feed to gain) Day 0-14 | Day 0-21 | Day 14-21 | Day 0-35 | Day 0-42 |
|---|---|---|---|---|---|
| Phage in feed | 1.680 | $1.777^{ABC}$ | $1.868^{B}$ | $1.841^{C}$ | $2.089^{C}$ |
| SEM[2] | .045 | .051 | .081 | .047 | .039 |
| Pr > F | .1359 | .0002 | .0001 | .0001 | .0001 |

[1]LSMEANS were provided for each treatment. The treatment group included a control. Challenged control, BMD 50 g/ton as a medicated control, oral gavaged phage, phage provided via water and phage provided via feed. The bacteriophage used was Intralytix *C. perfringens* Phage Cocktail - 4.8 × $10^9$ pfu/ml. On Day 14, all the birds were orally inoculated with a coccidial inoculums containing approximately 5,000 oocysts of *E. maxima* per bird. All groups were challenged with *Clostridium perfringens* on Days 18, 19, and 20. Oral Administration of phage cocktail via gavage drinking water and feed application will occurred on days 17, 18, 19, 20, and 21.

[2]Standard error of the LSMEANS $^{A,B,C,D}$Means within columns with different subscripts are significantly different.

TABLE 14

Delivery Routes of Bacteriophage on mortality and lesion scores of broiler chickens challenged with necrotic enteritis

| Treatment[1] | Mortality (%)[2] Total include all causes Day 0-21 | Day 0-35 | Day 0-42 | Necrotic Enteritis Day 0-42 | Necrotic Enteritis lesion scores[3] |
|---|---|---|---|---|---|
| Control | $2.67^{CD}$ | $2.67^{D}$ | $4.00^{D}$ | $0^{D}$ | $0^{B}$ |
| Challenged control | $41.33^{A}$ | $66.00^{A}$ | $66.67^{A}$ | $64.00^{A}$ | $.9^{A}$ |
| BMD control | $24.67^{B}$ | $51.33^{B}$ | $53.33^{B}$ | $50.00^{B}$ | $1.1^{A}$ |
| Gavaged phage | $10.00^{C}$ | $16.67^{C}$ | $18.00^{C}$ | $14.00^{C}$ | $.1^{B}$ |
| Phage in water | $.67^{D}$ | $67^{D}$ | $3.33^{D}$ | $0^{D}$ | $.1^{B}$ |
| Phage in feed | $2.00^{CD}$ | $3.33^{D}$ | $5.33^{D}$ | $.66^{D}$ | $.4^{B}$ |
| SEM[4] | 2.97 | 2.71 | 2.81 | 2.76 | .2 |
| Pr > F | .0001 | .0001 | .0001 | .0001 | .0006 |

[1]LSMEANS were provided for each treatment. The treatment group included a control. Challenged control, BMD 50 g/ton as a medicated control, oral gavaged phage, phage provided via water and phage provided via feed. The bacteriophage used was Intralytix *C. perfringens* Phage Cocktail - 4.8 × $10^9$ pfu/ml. On Day 14, all the birds were orally inoculated with a coccidial inoculums containing approximately 5,000 oocysts of *E. maxima* per bird. All groups were challenged with *Clostridium perfringens* on Days 18, 19, and 20. Oral Administration of phage cocktail via gavage drinking water and feed application will occurred on days 17, 18, 19, 20, and 21.

[2]Standard error of the LSMEANS

[3]On Day 22, scoring was based on a 0 to 3 score, with 0 being normal and 3 being the most severe.

[4]Standard error of the LSMEANS $^{A,B,C,D}$Means within columns with different subscripts are significantly different.

The non-challenged control (Treatment 1) had the numerically highest (102 grams per bird per day) feed intake and this was significantly (p>0.05) more than Treatment 5 (84 grams per bird per day). Although the means comparison was not significant (p>0.05), Treatment 8 had the numerically best FCR (1.477) of the Phage treated groups and equal to the performance of the non-challenged control.

Conclusions:

1. A successful *Clostridium perfringens* (Cp) challenge was achieved. The positive control had 25.9% of the birds die from Necrotic Enteritis compared to the negative control (0.0%).
2. Oral Gavage of Test Article to birds on the day of challenge (Day 14) and for the next four days significantly reduced mortality due to NE. Growth performance in this group was numerically equivalent to the Non-Challenged control.
3. Two of the three "In ovo" treatments had numerically reduced NE mortality (9.6 and 14.8%) when compared to the Challenged control (25.9%).
4. Oral Gavage of Test Article prior to challenge was ineffective in preventing NE mortality due to Cp challenge.

5. Spray of Test Article to chicks at the hatchery did not significantly (p>0.05) reduce NE mortality from Cp challenge.
6. The precision of this trial was reduced by several factors including fewer birds being assigned to pens at day old than specified in the protocol and high early non-challenged related mortality.

Example 5

Sequence Analysis of *C. perfringens* Bacteriophage

Media:

Brain Heart Infusion (BHI) broth or BHI agar supplemented with 250 mg/L cycloserine was used to grow all *C. perfringens* isolates. Luria-Bertani (LB) broth and LB agar was used to grow all aerobic strains. All media were obtained from EMD Chemicals, Gibbstown, N.J.

Microoganisms:

*Clostridium perfringens* strains were from Intralytix Inc. Culture Collection, Baltimore, Md. As part of the collection process, isolates were checked for purity and frozen at −80° C. in 30% glycerol. Most of the work was performed in an anaerobic chamber (Plas-Labs, Lansing, Mich.), that contained a 90% $N_2$-5% $H_2$-5% $CO_2$ atmosphere. *Escherichia coli, Listeria monocytogenes, Salmonella enteric*, and *Pseudomonas aeruginosa* strains were from the Intralytix Inc. Culture Collection and all were grown aerobically.

Bacteriophage:

All bacteriophage were isolated from environmental water sources.

Phage DNA Isolation:

DNA from each batch of bacteriophage was isolated by standard phenol-chloroform extraction method. Proteinase K (200 μg/ml) and RNAse A (1 μg/ml) were added to phage samples with titer≥$1\times10^9$ PFU/ml and incubated at 37° C. for 30 minutes followed by 56° C. for an additional 30 minutes. SDS/EDTA was added to a final concentration of 0.1% and 5 mM respectively and incubated at room temperature for 5 minutes. The samples were extracted once with buffered phenol, once with phenol-chloroform and once with chloroform. Phage DNA was ethanol precipitated and resuspended in 10 mM Tri-HCl (pH 8.0)-0.1 mM EDTA (TE) buffer.

Phage Sequencing:

The DNA from each of the phages was sequenced using standard automated sequencing methods.

Sequence Analysis:

To identify the predicted open reading frames (ORFs) WPA uses a combination of CRITICA (1) and GLIMMER (2). The results from these programs are combined and the optimal reading frames are extracted from the combined data set.

Each of the two programs uses different algorithms for identifying open reading frames, and each has its benefits and drawbacks. However, by combining the output from both tools WPA is able to optimize the predicted ORFs that they can identify.

WPA uses an automated annotation system in which assignments are generated primarily by sequence similarity searches between the de novo indentified ORFs and other ORFs in their databases. In this case, the BLAST algorithm was used to compare predicted protein sequences for the annotation. In addition to the publicly available databases for comparison WPA has a phage database that contains approximately 400 phage genomes which they feel represents the best phage dataset available.

Following the automated annotation and assignment phase, the assignments for each genome are manually curated by Intralytix to see if any of the 17 undesirable genes (Table 15) are present.

TABLE 15

List of undesirable genes encoded in the bacteriophage genomes

| Toxin and its Encoding Gene | Bacterial Pathogen |
|---|---|
| Enterotoxin A (entA) | *Staphyloccocus aureus* |
| Enterotoxin A (sea, sel) | *Staphyloccocus* |
| Enterotoxin A (sea) | *Staphyloccocus aureus* |
| Staphylokinase (sak) | *Staphyloccocus aureus* |
| Enterotoxin P (sep) | *Staphyloccocus aureus* |
| Exfoliative toxin A (eta) | *Staphyloccocus aureus* |
| Diptheria toxin (tox) | *Corynebacterium diptheriae* |
| Shiga toxins (stx1, 2) | *Escherichia coli* |
| Cytotoxin (ctx) | *Pseudomonas aeruginosa* |
| Cholera toxin (ctxA) | *Vibrio cholerae* |
| Cholera toxin (ctxB) | *Vibrio cholera* |
| Zona occludens toxin (zot) | *Vibrio cholerae* |
| Neurotoxin (C1) | *Clostridium botulinum* |
| Enterohaemolysin (hly) | *Escherichia coli* |
| Streptococcal enterotoxin A (speA) | *Streptococcus pyrogenes* |
| Streptococcal enterotoxin C (speC) | *Streptococcus pyrogenes* |
| Streptococcal enterotoxin K(speK) | *Streptococcus pyrogenes* |

Five of the six phages were sequenced. The sequences of each of the five phage genomes were obtained and each predicted open reading frame identified in each genome (Table 16). Each of the predicted genes was annotated. None of the 17 undesirable genes (Table 15) were found in the genomes of any of the five phages for which sequences were available (Table 17).

TABLE 16

Number of predicted ORFs for each *C. perfringens*-specific bacteria.

| Phage | Number of Open Reading Frames (ORFs) |
|---|---|
| 1 | 67 |
| 2 | 77 |
| 3 | 69 |
| 4 | 47 |
| 5 | 67 |

Example 6

Use of a Water-Conditioning Agent in the Phage Cocktail

Phage cocktail INT-401 at a final concentration of $1\times10^7$ pfu/ml was placed into treated (containing 50 mM citrate-phosphate-thiosulfate (CTP) buffer, comprising about 40 mg sodium thiosulfate, 6.0 gm disodium phosphate (anhydrous), 1.1 gm citric acid (anhydrous) per liter of deioinized water, pH 7.0 (added at a 1:10 ratio to water) and untreated (distilled water) solutions containing bleach at the levels indicated in Table 18, and allowed to stand for one hour at room temperature. Samples were taken, and 10 microliters were spotted onto BHI agar medium containing lawns of *C. perfringens* ATCC 13124 and allowed to dry. Plates were incubated overnight at 37° C., and phage inactivation was scored by the absence of a lytic clearing zone visible on the bacterial lawn.

Results: The results in Table 18 demonstrated the thiosulfate-containing buffer was able to protect phage cocktail INT-401 against oxidation due to chlorine bleach exposure. This conditioning agent could therefore be applied to chlorinated water as a means to allow the phage cocktail to retain activity in a commercial poultry watering system.

TABLE 18

Water Conditioning Agent Allowing Protection of Phage Cocktail INT-401 in the Presence of Hypochlorite

| | Lysis Response vs. ATCC 13124 | |
|---|---|---|
| Hypochlorite concentration | Conditioned water | Unconditioned water |
| 0 | ++ | ++ |
| 0.5 | ++ | + |
| 1.0 | ++ | + |
| 2.0 | + | − |
| 4.0 | + | − |
| 6.0 | + | − |

Example 7

Treatment of *C. septicum* with INT-401

Seven *C. septicum* and two *C. perfringens* turkey isolates, associated with turkey dermatitis or related turkey disease complexes were received from Marion Morgan, University of Arkansas Dept. of Poultry Science, in meat broth. Strain ATCC 13124 (*C. perfringens*) was used as an internal control and was used from a frozen source from the Alpharma Animal Health Culture Collection, Chicago Heights, Ill. Strains were sub-cultured; 0.1 ml of broth into 9 ml Wilkins-Chalgren medium, and Wilkens-Chalgren and supplemented Mueller-Hinton agar, followed by overnight growth at 37° C. Once colonies were observed, at least 10 representative colonies of each strain were transferred into 1 ml sterile saline, to a uniform turbidity corresponding to about $10^8$-$10^9$ cfu/ml cell density. The saline suspensions were inoculated at 0.1 ml per plate and evenly distributed to one plate each of unsupplemented Wilkins-Chalgren and Mueller-Hinton agar (supplemented with 0.25% w/v glucose). Commercial antibiotic disks were then placed onto the surface of each plate, along with 15 μl spots of INT-401 phage cocktail, (ca. $10^8$ pfu phage/ml). The spots were allowed to completely absorb onto the plate surface. All plates were then incubated at 37° C. in an anaerobic vessel (using BBL Gas-Pak® to generate anaerobiosis). Zones of inhibition were measured (in millimeters) for each antibiotic, and evaluation of lysis of bacteria due to INT-401 phage was recorded for each strain. Table 17 summarizes the results of the study.

TABLE 17

Lysis response of *Clostridium* spp. to Phage Cocktail INT-401 on Two Culture Media Formulations.

| Strain | Species | Lysis from INT-401 (Wilkins-Chalgren) | Lysis from INT-401 (Mueller-Hinton) |
|---|---|---|---|
| 08-114 | *C. septicum* | + | + |
| 08-121 | *C. septicum* | − | (+) |
| 08-126 | *C. septicum* | (+) | − |
| 08-183 | *C. septicum* | (+) | (+) |
| 08-196 | *C. septicum* | (+) | (+) |
| 08-205 | *C. septicum* | (+) | − |
| 09-03 | *C. septicum* | + | + |
| 08-41 | *C. perfringens* | + | + |

TABLE 17-continued

| Lysis response of *Clostridium* spp. to Phage Cocktail INT-401 on Two Culture Media Formulations. | | | |
|---|---|---|---|
| Strain | Species | Lysis from INT-401 (Wilkins-Chalgren) | Lysis from INT-401 (Mueller-Hinton) |
| 08-146 | *C. perfringens* | + | + |
| ATCC 13124 (control) | *C. perfringens* | + | + |

Responses scores:
+ clear lysis of entire challenge spot;
− no lysis observed;
(+) partial lysis (clear individual plaques or less turbid zone observed).

The results show that disease-associated poultry *C. septicum* strains may be lysed by phage cocktail INT-401. In this case 2/7 strains demonstrated clear-cut lysis comparable to *C. perfringens* controls, and all 7 strains showing some response to the product. Some differences between culturing medium were noted.

Example 8

Bacterial Lysis Using Both Phage and Antibiotic Treatments

Antibiotic Enhancement of Phage Lysis:

Lawns of overnight growth of host strain CP8, lysed by 4/5 component phages of INT-401, were streaked onto BHI and Shaedler agar medium, and at least 3 10 μl spots of −1, and −2 dilutions of INT-401 phage were placed onto the surface, and allowed to dry. Subsequently, commercial disks of bacitracin (10 microgram, Hardy Diagnostics) and chlortetracycline (30 microgram, Hardy Diagnostics) were placed adjacent to the phage spots at a distance of 1-3 mm. Control spots and control antibiotic disks were placed >15 mm apart. The plates were then incubated overnight at 37° C., in a commercial anaerobic jar, and data were recorded for zones of inhibition present/absent and interactive effects, if any.

Strain CP-8 demonstrated an enhanced lysis effect at the intersection of INT-401 plus antibiotics chlortetracycline or bacitracin. The on-plate regions of overlapping interaction of both phage and antibiotic against the *Clostridium* bacteria lawn, had somewhat larger (by 1-3 mm) clearing areas, with no visible encroaching bacterial growth on the edges, having a distinctive and superior clearing zone with clean, straight edges. The control spots or disks had visibly or microscopically less distinctively clear edges, and occasional visible single colonies encroaching on the edges (these have borderline, lower concentrations present thus will allow some growth of some bacteria). This result shows that the phage cocktail product INT-401 and antibiotics, both of which are inhibitory of *Clostridium* spp. (and in particular *Clostridium perfringens*) and for antibiotics which are approved and are routinely used for growth promotion, disease prevention, disease control, or disease treatment purposes, have demonstrably compatible activities. Both phage and antibiotics can kill or inhibit bacteria by different mechanisms and modes of action. This test shows to a significant degree that the two mechanisms do not interfere with each other and appear to provide complementary killing activity. Multiple antibiotics and phage mixtures have at least an additive effect and in several cases show synergistic activities against bacteria, using qualitative or quantitative methodology

Example 9

INT-401 Treatment Versus Antibiotic Resistant *C. perfringens* Strains

Antibiotic-Resistant *Clostridium perfringens* Test:

Strains of *C. perfringens*, were grown and subsequently challenged, using spots (−1 or −2 dilutions) of phage cocktail INT-401, according to standardized methods on BHI agar medium. Both antibiotic-sensitive controls (ATCC reference and host strains), as well as animal-origin strains in the Alpharma Animal Health culture collection were tested. The strains were identifiable by previously measured, notable antibiotic resistances: 10 pan-susceptible strains (sensitive to all tested antibiotics), 6 bacitracin-tolerant strains; of which 3 had MIC>50 ppm, and 2 macrolide-resistant (MIC>32 for tylosin tartrate) strains. Data concerning INT-401 lysis were recorded based on observation of visible lysis on lawns following overnight incubation. Table 17 summarizes the results, showing lysis patters versus examples of antibiotic pan-susceptible (control), and specific antibiotic-resistant animal strains of *C. perfringens*.

TABLE 17

| Lysis response of Antibiotic-tolerant or -sensitive, animal *Clostridium perfringens* strains to Phage Cocktail INT-401. | | |
|---|---|---|
| Strain | Defined Antibiotic Resistance (MIC, ppm) | Lysis from INT-401 (BHI agar) |
| ATCC 3624 | bac. tyl. (<2), S | + |
| ATCC 13124 (control) | bac. tyl.(<2), S | + |
| ATCC 9856 | bac. tyl. (<2), S | + |
| Warren | bac (50) | + |
| G84239 | bac (4) | + |
| TO4213 | bac.(2) | − |
| M3836 | bac.(4) | + |
| CL3801 | bac.(50) | − |
| EV3839 | bac.(50) | + |
| N84236 | tyl (≥32) | + |
| CH4225 | tyl (≥32) | + |
| JGS4029 | bac. tyl.(<2), S | − |
| JGS4027 | bac. tyl.(<2), S | + |
| JGS4026 | bac. tyl.(<2), S | + |
| JGS4016 | bac. tyl.(<2), S | + |
| JGS4057 | bac. tyl.(<2), S | − |
| JGS4048 | bac. tyl.(<2), S | − |
| JGS4036 | bac. tyl.(<2), S | + |

S = Pan susceptible to all tested antibiotics. bac-bacitracin, tyl, tylosin (and other macrolide cross-resistant class antibiotics including lincomycin and erythromycin)

In summary, 7/10 of pan-susceptible strains, compared with 4/6 total bacitracin resistant (2/3 highly bacitracin-resistant), and 2/2 highly macrolide-resistant (tylosin-resistant) strains were lysed by the INT-401 cocktail challenge. The results show that phage can lyse antibiotic-resistant bacteria to the same or greater degree as antibiotic-susceptible types.

The terms “first”, “second”, and the like herein, do not denote any order, quantity, or importance, but rather are used to distinguish one element from another, and the terms “a” and “an” herein do not denote a limitation of quantity, but rather denote the presence of at least one of the referenced item. All ranges disclosed herein are inclusive and combinable.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated by reference in their entirety.

TABLE 17

Annotations of all predicted genes for each *C. perfringens*-specific bacteriophage genome

| Gene ID | Annotated Function |
|---|---|
| CPAS-7 | |
| 1 | Presumed portal vertex protein |
| 2 | Ring-infected erythrocyte surface antigen |
| 3 | Hypothetical protein |
| 4 | Hypothetical protein |
| 5 | FKBP-type peptidyl-prolyl cis-trans isomerase (trigger factor) |
| 6 | Isocitrate dehydrogenase kinase/phosphatase |
| 7 | Phage-like element PBSX protein xkdH |
| 8 | Phase 1 flagellin |
| 9 | Type I restriction-modification system restriction subunit (EC 3.1.21.3) |
| 10 | Sarcosine oxidase, alpha subunit |
| 11 | Hypothetical protein |
| 12 | Phage-like element PBSX protein xkdK |
| 13 | Phage-like element PBSX protein xkdM |
| 14 | Hypothetical protein |
| 15 | Hypothetical protein |
| 16 | Phage protein |
| 17 | Hypothetical protein |
| 18 | Phage-like element PBSX protein xkdQ |
| 19 | Ribosomal protein S4 and related proteins |
| 20 | Phage-like element PBSX protein xkdS |
| 21 | Hypothetical protein |
| 22 | Phage-like element PBSX protein xkdT |
| 23 | Tail fiber |
| 24 | Heat shock protein 90 |
| 25 | Hypothetical protein |
| 26 | Bacteriocin uviB precursor |
| 27 | N-acetylmuramoyl-L-alanine amidase (EC 3.5.1.28) |
| 28 | ABC transporter, permease protein |
| 29 | No hits |
| 30 | Transposase |
| 31 | DNA repair protein RadA |
| 32 | Transcriptional regulator |
| 33 | Hypothetical protein |
| 34 | Hypothetical protein |
| 35 | Thymidine kinase (EC 2.7.1.21) |
| 36 | Tryptophanyl-tRNA synthetase (EC 6.1.1.2) |
| 37 | CMP-binding factor |
| 38 | 3-isopropylmalate dehydratase large subunit (EC 4.2.1.33) |
| 39 | DNA ligase |
| 40 | Putative penicillin-binding protein |
| 41 | Signal transducer and activator of transcription 1 |
| 42 | Chemotaxis protein CHED |
| 43 | Gramicidin S synthetase I (EC 5.1.1.11) |
| 44 | ABC transporter ATP-binding protein |
| 45 | Putative ATP-dependent DNA helicase |
| 46 | DNA polymerase I |
| 47 | Hypothetical protein |
| 48 | Hypothetical protein |
| 49 | Phenylalanyl-tRNA synthetase beta chain |
| 50 | Terminase large subunit |
| 51 | Terminase small subunit |
| 52 | Hypothetical protein |
| 53 | CobT protein |
| 54 | Putative chromosome segregation protein, SMC ATPase superfamily |
| 55 | Deoxycytidylate deaminase (EC 3.5.4.12) |

TABLE 17-continued

Annotations of all predicted genes for each *C. perfringens*-specific bacteriophage genome

| Gene ID | Annotated Function |
|---|---|
| 56 | aceE; pyruvate dehydrogenase e1 component oxidoreductase protein |
| 57 | Hypothetical protein |
| 58 | Hypothetical protein |
| 59 | Aspartic acid-rich protein aspolin2 |
| 60 | CDEP |
| 61 | Nucleolin |
| 62 | Peptide ABC transporter, ATP-binding protein |
| 63 | GTP-binding protein SAR1 |
| 64 | gp56 dCTPase |
| 65 | Hypothetical protein |
| 66 | Homeobox-leucine zipper protein |
| 67 | DNA repair protein recN |
| CPAS-16 | |
| 1 | Developmentally regulated GTP-binding protein 1 |
| 2 | Presumed portal vertex protein |
| 3 | Ring-infected erythrocyte surface antigen |
| 4 | Hypothetical protein |
| 5 | Hypothetical protein |
| 6 | FKBP-type peptidyl-prolyl cis-trans isomerase (trigger factor) |
| 7 | Isocitrate dehydrogenase kinase/phosphatase |
| 8 | Phage-like element PBSX protein xkdH |
| 9 | High-affinity potassium transporter |
| 10 | Sarcosine oxidase, alpha subunit |
| 11 | Hypothetical protein |
| 12 | Phage-like element PBSX protein xkdK |
| 13 | Phage-like element PBSX protein xkdM |
| 14 | Hypothetical protein |
| 15 | Hypothetical protein |
| 16 | Phage protein |
| 17 | Hypothetical protein |
| 18 | Phage-like element PBSX protein xkdQ |
| 19 | Ribosomal protein S4 and related proteins |
| 20 | Phage-like element PBSX protein xkdS |
| 21 | Hypothetical protein |
| 22 | Phage-like element PBSX protein xkdT |
| 23 | Tail fiber |
| 24 | Heat shock protein 90 |
| 25 | Hypothetical protein |
| 26 | Bacteriocin uviB precursor |
| 27 | N-acetylmuramoyl-L-alanine amidase (EC 3.5.1.28) |
| 28 | Enterotoxin |
| 29 | Membrane protein |
| 30 | No hits |
| 31 | Thymidylate synthase (EC 2.1.1.45) |
| 32 | Heat shock protein (dnaJ-2) |
| 33 | Hypothetical protein |
| 34 | DNA polymerase I |
| 35 | DNA polymerase I |
| 36 | Putative ATP-dependent DNA helicase |
| 37 | ABC transporter ATP-binding protein |
| 38 | Terminase large subunit |
| 39 | Terminase small subunit |
| 40 | CobT protein |
| 41 | Putative chromosome segregation protein, SMC ATPase superfamily |
| 42 | Deoxycytidylate deaminase (EC 3.5.4.12) |
| 43 | aceE; pyruvate dehydrogenase e1 component oxidoreductase protein |
| 44 | Hypothetical protein |
| 45 | Hypothetical protein |
| 46 | Genomic DNA, chromosome 3, BAC clone: F1D9 |
| 47 | SWF/SNF family helicase |
| 48 | Aspartic acid-rich protein aspolin2 |
| 49 | CDEP |
| 50 | Nucleolin |
| 51 | Hypothetical protein |
| 52 | Putative reductase |
| 53 | Hypothetical protein |
| 54 | Hypothetical protein |
| 55 | Hypothetical protein |
| 56 | Tail fiber |
| 57 | gp56 dCTPase |
| 58 | Acetate kinase (EC 2.7.2.1) |

TABLE 17-continued

| Annotations of all predicted genes for each *C. perfringens*-specific bacteriophage genome | |
|---|---|
| Gene ID | Annotated Function |
| 59 | GTP-binding protein SAR1 |
| 60 | Peptide ABC transporter, ATP-binding protein |
| 61 | Cytochrome b (EC 1.10.2.2) |
| 62 | Homeobox-leucine zipper protein |
| 63 | DNA repair protein recN |
| 64 | Transposase |
| 65 | DNA repair protein RadA |
| 66 | Exonuclease I |
| 67 | Transcriptional regulator |
| 68 | Hypothetical protein |
| 69 | Thymidine kinase (EC 2.7.1.21) |
| 70 | Tryptophanyl-tRNA synthetase (EC 6.1.1.2) |
| 71 | CMP-binding factor |
| 72 | 3-isopropylmalate dehydratase large subunit (EC 4.2.1.33) |
| 73 | DNA ligase |
| 74 | Putative penicillin-binding protein |
| 75 | Signal transducer and activator of transcription 1 |
| 76 | Chemotaxis protein CHED |
| 77 | Gramicidin S synthetase I (EC 5.1.1.11) |
| CPAS-15 | |
| 1 | Gramicidin S synthetase I (EC 5.1.1.11) |
| 2 | Chemotaxis protein CHED |
| 3 | Signal transducer and activator of transcription 1 |
| 4 | Putative penicillin-binding protein |
| 5 | DNA ligase |
| 6 | 3-isopropylmalate dehydratase large subunit (EC 4.2.1.33) |
| 7 | CMP-binding factor |
| 8 | Tryptophanyl-tRNA synthetase (EC 6.1.1.2) |
| 9 | Thymidine kinase (EC 2.7.1.21) |
| 10 | Hypothetical protein |
| 11 | Hypothetical protein |
| 12 | Transcriptional regulator |
| 13 | Exonuclease I |
| 14 | DNA repair protein RadA |
| 15 | Transposase |
| 16 | ABC transporter ATP-binding protein |
| 17 | Y56A3A.29a protein |
| 18 | DNA polymerase I |
| 19 | DNA polymerase I |
| 20 | Thymidylate synthase (EC 2.1.1.45) |
| 21 | Hypothetical protein |
| 22 | SWF/SNF family helicase |
| 23 | Aspartic acid-rich protein aspolin2 |
| 24 | CDEP |
| 25 | Hypothetical protein |
| 26 | Terminase large subunit |
| 27 | Terminase small subunit |
| 28 | CobT protein |
| 29 | Putative chromosome segregation protein, SMC ATPase superfamily |
| 30 | Deoxycytidylate deaminase (EC 3.5.4.12) |
| 31 | aceE; pyruvate dehydrogenase e1 component oxidoreductase protein |
| 32 | Hypothetical protein |
| 33 | Hypothetical protein |
| 34 | DNA repair protein recN |
| 35 | Homeobox-leucine zipper protein |
| 36 | Hypothetical protein |
| 37 | No hits |
| 38 | Hypothetical protein |
| 39 | N-acetylmuramoyl-L-alanine amidase (EC 3.5.1.28) |
| 40 | Bacteriocin uviB precursor |
| 41 | Hypothetical protein |
| 42 | Heat shock protein 90 |
| 43 | Tail fiber |
| 44 | PROBABLE SUCCINYL-COA SYNTHETASE BETA CHAIN PROTEIN |
| 45 | Phage-like element PBSX protein xkdT |
| 46 | Hypothetical protein |
| 47 | Phage-like element PBSX protein xkdS |
| 48 | Ribosomal protein S4 and related proteins |
| 49 | Phage-like element PBSX protein xkdQ |
| 50 | Hypothetical protein |
| 51 | Phage protein |

TABLE 17-continued

| Annotations of all predicted genes for each *C. perfringens*-specific bacteriophage genome | |
|---|---|
| Gene ID | Annotated Function |
| 52 | Phage protein |
| 53 | Hypothetical protein |
| 54 | Hypothetical protein |
| 55 | Phage-like element PBSX protein xkdM |
| 56 | Phage-like element PBSX protein xkdK |
| 57 | Hypothetical protein |
| 58 | Sarcosine oxidase, alpha subunit |
| 59 | High-affinity potassium transporter |
| 60 | Phage-like element PBSX protein xkdH |
| 61 | Putative nodulation protein |
| 62 | Isocitrate dehydrogenase kinase/phosphatase |
| 63 | FKBP-type peptidyl-prolyl cis-trans isomerase (trigger factor) |
| 64 | Hypothetical protein |
| 65 | Hypothetical protein |
| 66 | Ring-infected erythrocyte surface antigen |
| 67 | Presumed portal vertex protein |
| 68 | GTP-binding protein SAR1 |
| 69 | Hypothetical protein |
| CPLV-42 | |
| 1 | Hypothetical protein |
| 2 | Ribosomal protein S4 and related proteins |
| 3 | Hypothetical protein |
| 4 | F14H3.11 protein |
| 5 | Myosin heavy chain, cardiac muscle beta isoform |
| 6 | Holin |
| 7 | N-acetylmuramoyl-L-alanine amidase (EC 3.5.1.28) |
| 8 | Developmentally regulated GTP-binding protein 1 |
| 9 | Hypothetical protein |
| 10 | DNA internalization-related competence protein ComEC/Rec2 |
| 11 | Phage-related protein |
| 12 | Antirepressor |
| 13 | Phage protein |
| 14 | Hypothetical protein |
| 15 | Excinuclease ABC subunit B |
| 16 | Putative oxidoreductase protein |
| 17 | DNA topoisomerase I (EC 5.99.1.2) |
| 18 | Imidazole glycerol phosphate synthase subunit hisF (EC 4.1.3.—) |
| 19 | Methyl-accepting chemotaxis protein |
| 20 | Hypothetical protein |
| 21 | Aminomethyltransferase (EC 2.1.2.10) |
| 22 | Hypothetical protein |
| 23 | Hypothetical protein |
| 24 | Hypothetical protein |
| 25 | Hypothetical protein |
| 26 | Hypothetical protein |
| 27 | Hypothetical protein |
| 28 | DNA polymerase III, subunit beta |
| 29 | Terminase large subunit |
| 30 | lin2585 |
| 31 | Portal protein |
| 32 | Genomic DNA, chromosome 3, BAC clone: F1D9 |
| 33 | Deoxyguanosinetriphosphate triphosphohydrolase (dgtP) |
| 34 | Virulence-associated protein E |
| 35 | Hypothetical protein |
| 36 | 3'-phosphoadenosine 5'-phosphosulfate sulfotransferase (PAPS reductase)/FAD synthetase and related enzymes, COG0175 |
| 37 | Phosphoadenosine phosphosulfate reductase (EC 1.8.4.8) |
| 38 | Hypothetical protein |
| 39 | Hypothetical protein |
| 40 | WRKY transcription factor 22 |
| 41 | D-threonine dehydrogenase |
| 42 | Hypothetical protein |
| 43 | Hypothetical protein |
| 44 | Transcriptional regulator |
| 45 | Single-strand binding protein |
| 46 | Hypothetical protein |
| 47 | Sensor histidine kinase |
| CPAS-12 | |
| 1 | Presumed portal vertex protein |
| 2 | Ring-infected erythrocyte surface antigen |
| 3 | Hypothetical protein |
| 4 | Hypothetical protein |

TABLE 17-continued

| Gene ID | Annotated Function |
|---|---|
| | Annotations of all predicted genes for each *C. perfringens*-specific bacteriophage genome |
| 5 | FKBP-type peptidyl-prolyl cis-trans isomerase (trigger factor) |
| 6 | Isocitrate dehydrogenase kinase/phosphatase |
| 7 | Phage-like element PBSX protein xkdH |
| 8 | High-affinity potassium transporter |
| 9 | Sarcosine oxidase, alpha subunit |
| 10 | Hypothetical protein |
| 11 | Phage-like element PBSX protein xkdK |
| 12 | Phage-like element PBSX protein xkdM |
| 13 | Hypothetical protein |
| 14 | Hypothetical protein |
| 15 | Phage protein |
| 16 | Hypothetical protein |
| 17 | Phage-like element PBSX protein xkdQ |
| 18 | Ribosomal protein S4 and related proteins |
| 19 | Phage-like element PBSX protein xkdS |
| 20 | Hypothetical protein |
| 21 | Phage-like element PBSX protein xkdT |
| 22 | Tail fiber |
| 23 | Heat shock protein 90 |
| 24 | Hypothetical protein |
| 25 | Bacteriocin uviB precursor |
| 26 | N-acetylmuramoyl-L-alanine amidase (EC 3.5.1.28) |
| 27 | ABC transporter, permease protein |
| 28 | No hits |
| 29 | Gramicidin S synthetase I (EC 5.1.1.11) |
| 30 | Chemotaxis protein CHED |
| 31 | Signal transducer and activator of transcription 1 |
| 32 | Putative penicillin-binding protein |
| 33 | DNA ligase |
| 34 | 3-isopropylmalate dehydratase large subunit (EC 4.2.1.33) |
| 35 | CMP-binding factor |
| 36 | Tryptophanyl-tRNA synthetase (EC 6.1.1.2) |
| 37 | Thymidine kinase (EC 2.7.1.21) |
| 38 | Nucleolin |
| 39 | Transcriptional regulator |
| 40 | DNA repair protein RadA |
| 41 | Transposase |
| 42 | Hypothetical protein |
| 43 | Thymidylate synthase (EC 2.1.1.45) |
| 44 | Heat shock protein (dnaJ-2) |
| 45 | DNA polymerase I |
| 46 | Putative ATP-dependent DNA helicase |
| 47 | ABC transporter ATP-binding protein |
| 48 | Terminase large subunit |
| 49 | Terminase small subunit |
| 50 | CobT protein |
| 51 | Putative chromosome segregation protein, SMC ATPase superfamily |
| 52 | Deoxycytidylate deaminase (EC 3.5.4.12) |
| 53 | aceE; pyruvate dehydrogenase e1 component oxidoreductase protein |
| 54 | Hypothetical protein |
| 55 | Hypothetical protein |
| 56 | Genomic DNA, chromosome 3, BAC clone: F1D9 |
| 57 | SWF/SNF family helicase |
| 58 | Aspartic acid-rich protein aspolin2 |
| 59 | CDEP |
| 60 | Nucleolin |
| 61 | Alpha/beta hydrolase fold: Esterase/lipase/thioesterase family . . . |
| 62 | Normocyte-binding protein 1 |
| 63 | Hypothetical protein |
| 64 | DNA repair protein recN |
| 65 | Homeobox-leucine zipper protein |
| 66 | Hypothetical protein |
| 67 | gp56 dCTPase |

We claim:

1. A purified bacteriophage preparation for reducing mortality in poultry due to *C. perfringens* infections comprising four or more *C. perfringens*-specific bacteriophage selected from the group consisting of CPAS-7 accession number PTA-8478, CPAS-12 accession number PTA-8479, CPAS-15 accession number PTA-8480, CPAS-16 accession number PTA-8481 and CPLV-42 accession number PTA-8483, wherein each bacteriophage has lytic activity against at least 5 strains of a *Clostridium* species and a citrate-phosphate-thiosulfate buffer.

2. The purified bacteriophage preparation of claim 1 wherein the *Clostridium* species is *Clostridium septicum.*

3. The purified bacteriophage preparation of claim 1 wherein the *Clostridium* species is *Clostridium difficile.*

4. A purified bacteriophage preparation for reducing mortality in poultry due to *C. perfringens* infections comprising four or more *C. perfringens*-specific bacteriophage selected from the group consisting of CPAS-7 accession number PTA-8478, CPAS-12 accession number PTA-8479, CPAS-15 accession number PTA-8480, CPAS-16 accession number PTA-8481 and CPLV-42 accession number PTA-8483, wherein each bacteriophage has lytic activity against at least 5 strains of a *Clostridium* species which are antibiotic resistant and a citrate-phosphate-thiosulfate buffer.

5. A composition comprising purified bacteriophage preparation for reducing mortality in poultry due to *C. perfringens* infections comprising four or more *C. perfringens*-specific bacteriophage selected from the group consisting of CPAS-7 accession number PTA-8478, CPAS-12 accession number PTA-8479, CPAS-15 accession number PTA-8480, CPAS-16 accession number PTA-8481 and CPLV-42 accession number PTA-8483, wherein each bacteriophage has lytic activity against at least 5 strains of a *Clostridium* species and an antibiotic and a citrate-phosphate-thiosulfate buffer.

6. The composition of claim 5 wherein the antibiotic is bacitracin.

7. The composition of claim 6 wherein the antibiotic is chlortetracycline.

8. The purified bacteriophage preparation of claim 1 wherein the four or more *C. perfringens*-specific bacteriophage are CPAS-12 accession number PTA-8479, CPAS-15 accession number PTA-8480, CPAS-16 accession number PTA-8481 and CPLV-42 accession number PTA-8483.

9. The purified bacteriophage preparation of claim 1 wherein the four or more *C. perfringens*-specific bacteriophage are CPAS-7 accession number PTA-8478, CPAS-12 accession number PTA-8479, CPAS-15 accession number PTA-8480, CPAS-16 accession number PTA-8481 and CPLV-42 accession number PTA-8483.

10. The composition of claim 5 wherein the purified bacteriophage preparation comprises CPAS-12 accession number PTA-8479, CPAS-15 accession number PTA-8480, CPAS-16 accession number PTA-8481 and CPLV-42 accession number PTA-8483.

11. The composition of claim 5 wherein the purified bacteriophage preparation comprises CPAS-7 accession number PTA-8478, CPAS-12 accession number PTA-8479, CPAS-15 accession number PTA-8480, CPAS-16 accession number PTA-8481 and CPLV-42 accession number PTA-8483.

* * * * *